(12) United States Patent
Lizardi

(10) Patent No.: US 6,287,824 B1
(45) Date of Patent: Sep. 11, 2001

(54) MOLECULAR CLONING USING ROLLING CIRCLE AMPLIFICATION

(75) Inventor: Paul M. Lizardi, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/396,281

(22) Filed: Sep. 15, 1999

Related U.S. Application Data

(60) Provisional application No. 60/100,327, filed on Sep. 15, 1998.

(51) Int. Cl.[7] .............................. C12P 19/34; C12Q 1/68; Q01N 33/00; C07H 21/02; C07H 21/04
(52) U.S. Cl. ........................... 435/91.2; 435/6; 435/91.1; 436/94; 536/23.1; 536/24.3; 536/24.33
(58) Field of Search .............................. 435/6, 91.1, 91.2, 435/183, 320.1; 436/94; 536/23.1, 24.3, 24.33, 25.3

(56) References Cited

U.S. PATENT DOCUMENTS

| | | |
|---|---|---|
| 4,748,111 | 5/1988 | Dattagupat et al. . |
| 4,883,750 | 12/1989 | Whiteley et al. . |
| 4,965,188 | 10/1990 | Mullis et al. . |
| 4,994,373 | 2/1991 | Stavrianopoulos et al. . |
| 5,001,050 | 3/1991 | Blanco et al. . |
| 5,043,272 | 8/1991 | Hartley . |
| 5,130,238 | 7/1992 | Malek et al. . |
| 5,198,543 | 3/1993 | Blanco et al. . |
| 5,242,794 | 9/1993 | Norman et al. . |
| 5,273,638 | 12/1993 | Konrad et al. . |
| 5,328,824 | 7/1994 | Ward et al. . |
| 5,354,668 | 10/1994 | Auerbach . |
| 5,409,818 | 4/1995 | Davey et al. . |
| 5,412,087 | 5/1995 | McGall et al. . |
| 5,427,930 | 6/1995 | Birkenmeyer et al. . |
| 5,429,807 | 7/1995 | Matson et al. . |
| 5,455,166 | 10/1995 | Walker . |
| 5,510,270 | 4/1996 | Fodor et al. . |
| 5,521,065 | 5/1996 | Whiteley et al. . |
| 5,547,843 | 8/1996 | Studier et al. . |
| 5,591,609 | 1/1997 | Auerbach . |
| 5,614,389 | 3/1997 | Auerbach . |
| 5,614,390 | 3/1997 | McCaslin et al. . |
| 5,616,478 | 4/1997 | Chetverin et al. . |
| 5,629,158 | 5/1997 | Uhlen . |
| 5,629,179 | 5/1997 | Mierendorf et al. . |
| 5,714,320 | 2/1998 | Kool . |
| 5,733,733 | 3/1998 | Auerbach . |
| 5,794,714 | 8/1998 | Cantor et al. . |
| 5,854,033 | * 12/1998 | Lizardi .............................. 435/91.2 |
| 6,143,495 | * 11/2000 | Lizardi et al. ............................ 435/6 |

FOREIGN PATENT DOCUMENTS

| | | |
|---|---|---|
| 0128332 | * 12/1984 | (EP) . |
| 0356021 | 7/1989 | (EP) . |
| 0466520 | 1/1992 | (EP) . |
| 84173 | 2/1992 | (EP) . |
| 0505012 | 9/1992 | (EP) . |
| 0667393 | 8/1995 | (EP) . |
| 0678582 | 10/1995 | (EP) . |
| 0439182 | 4/1996 | (EP) . |
| 2 332 516 | 6/1999 | (GB) . |
| 4-262799 | 9/1992 | (JP) . |
| 4-304900 | 10/1992 | (JP) . |
| 91/80307 | 6/1991 | (WO) . |
| 92/01813 A1 | 2/1992 | (WO) . |
| 94/24312 A2 | 10/1994 | (WO) . |
| 95/03430 A1 | 2/1995 | (WO) . |
| 95/03432 A1 | 2/1995 | (WO) . |
| 95/22623 A1 | 8/1995 | (WO) . |
| 95/25180 A1 | 9/1995 | (WO) . |
| 95/35390 A1 | 12/1995 | (WO) . |
| 96/33207 A1 | 10/1996 | (WO) . |
| 97/19193 A2 | 5/1997 | (WO) . |
| 97/20948 | 6/1997 | (WO) . |
| 97/42346 A1 | 11/1997 | (WO) . |
| 97/43447 | 11/1997 | (WO) . |
| 98/14610 | 4/1998 | (WO) . |
| 98/39485 | 9/1998 | (WO) . |
| 99/53102 | 10/1999 | (WO) . |

OTHER PUBLICATIONS

Chen & Ruffner, "Amplification of closed circular DNA in vitro," *Nucleic Acids Res.* 26:1126–27 (1998).

Zhang, et al., "Amplification of target–specific, ligation–dependent circular probe," *Gene* 211:277–85 (1998).

Abravaya, et al., "Detection of point mutations with a modified ligase chain reaction (Gap–LCR)," *Nucleic Acids Res.* 23(4):675–682 (1995).

Aliotta, et al., "Thermostable Bst DNA polymerase I lacks a 3'—>5' proofreading exonuclease activity," *Genet Anal.* 12(5–6):185–95 (1996).

(List continued on next page.)

*Primary Examiner*—Ethan Whitenant
*Assistant Examiner*—Frank Lu
(74) *Attorney, Agent, or Firm*—Needle & Rosenberg, P.C.

(57) ABSTRACT

Disclosed are reagents and a method for efficient in vitro molecular cloning of nucleic acid molecules of interest. Because the method is entirely in vitro, it can be automated and scaled-up in ways that are not possible in cell-based molecular cloning. The method involves insertion of a nucleic acid molecule of interest in a linear vector to form a circular vector where one strand is continuous and the other strand is discontinuous. The continuous strand of the circular vector is then amplified by rolling circle replication, amplifying the inserted nucleic acid molecule in the process. The amplification is rapid and efficient since it involves a single, isothermic reaction that replicates the vector sequences exponentially. The amplification process is amenable to automation where multiple reactions are carried out simultaneously in a small area. The amplified nucleic acid can be used for any purpose and in any manner that nucleic acid cloned or amplified by known methods can be used. This includes sequencing, probing, restriction analysis, subcloning, transcription, hybridization or denaturation analysis, further amplified, and storage for future use or analysis.

45 Claims, 7 Drawing Sheets

OTHER PUBLICATIONS

Alves & Carr, "Dot blot detection of point mutations with adjacently hybridising synthetic oligonucleotide probes," *Nucl. Acids. Res.* 16:8723 (1988).

Arnold, et al., "Assay Formats Involving Acridinium–Ester–Labeled DNA Probes," *Clin. Chem.* 35(8): 1588–1594 (1989).

Barany, "Genetic disease detection and DNA amplification using cloned thermostable ligase," *Proc. Natl. Acad Sci. USA* 88: 189–193 (1991).

Beier & Hoheisel, "Versatile derivatisation of solid support media for covalent bonding on DNA–microchips," *Nucleic Acids Res.* 27(9):1970–7 (1999).

Bertina et al., "Mutation in blood coagulation factor V associated with resistance to activated protein C", *Nature* 369: 64–67 (1994).

Birkenmeyer & Mushahwar, "DNA probe amplification methods," *Journal of Virological Methods* 35:117–126 (1991).

Blanco & Salas, "Characterization and purification of a phage ø29–encoded DNA polymerase required for the initiation of replication," *Proc. Natl. Acad. Sci.* 81:5325–5329 (1984).

Blanco, et al., "Highly Efficient DNA Synthesis by the Phage ø29 DNA Polymerase," *Journal of Biological Chemistry* 264(15):8935–8940 (1989).

Blanco, et al., "Terminal protein–primed DNA amplification," *Proc. Natl. Acad. Sci.* 91:12198–202 (1994).

Boehmer & Lehman, "Herpes Simplex Virus Type 1 ICP8: Helix–Destabilizing Properties," *Journal of Virology* 67(2):711–715 (1993).

Bonaldo, et al., "Normalization and subtraction: two approaches to facilitate gene discovery," *Genome Res.* 6(9):791–806 (1996).

Broude, et al., "Enhanced DNA sequencing by hybridization," *Proc. Natl. Acad. Sci.* 91:3072–76 (1994).

Burgess & Jacutin, "A new photolabile protecting group for nucleotides," *Am. Chem Soc. Abstracts,* vol. 221, abstract 281 (1996).

Butler & Chamberlin, "Bacteriophage SP6–specific RNA Polymerase," *Journal of Biological Chemistry* 257:5772–5778 (1982).

Chatterjee, et al., "Cloning and overexpression of the gene encoding bacteriophage T5 DNA polymerase," *Gene* 97:13–19 (1991).

Chetverina & Chetverin, "Cloning of RNA molecules in vitro," *Nucl. Acids. Res.* 21:2349–53 (1993).

Daubendiek & Kool, "Generation of catalytic RNAs by rolling transcription of synthetic DNA nanocircles," *Nat Biotechnol.* 15(3):273–7 (1997).

Daubendiek, et al., "Rolling–circle RNA synthesis: Circular oligonucleotides as efficient substrates for T7 RNA polymerase," *J. Am. Chem. Soc.* 117:7818–19 (1995).

Davanloo, et al., "Cloning and expression of the gene for bacteriophage T7 RNA polymerase," *Proc. Natl. Acad. Sci. USA* 81:2035–2039 (1984).

Davis, et al., *Advanced Bacterial Genetics—A Manual for Genetic Engineering* (Cold Spring Harbor Laboratory, Cold Spring Harbor, N.Y., 1980).

Dynal, *Biomagnetic Techniques in Molecular Biology,* 1995.

Ernst, et al., "Cyanine dye labeling reagents for sulfhydryl groups," *Cytometry* 10:3–10 (1989).

Fire & Xu, "Rolling replication of short DNA circles," *Proc. Natl. Acad Sci. USA* 92:4641–4645 (1995).

Gasparro, et al., "Site–specific targeting of psoralen photoadducts with a triple helix–forming oligonucleotide: characterization of psoralen monoadduct and crosslink formation," *Nucleic Acids Research* 22(14):2845–2852 (1994).

Gerdes, et al., "Dynamic changes in the higher–level chromatin organization of specific sequences revealed by in situ hybridization to nuclear halos," *J Cell Biol.* 126(2):289–304 (1994).

Gunji, et al., "Correlation Between the Serum Level of Hepatitis C Virus RNA and Disease Activities in Acute and Chronic Hepatitis C," *Int. J. Cancer* 52(5):726–730 (1992).

Guo, et al., "Direct fluorescence analysis of genetic polymorphisms by hybridization with oligonucleotide arrays on glass supports," *Nucleic Acids Res.* 22(24):5456–5465 (1994).

Guo, et al., "Enhanced discrimination of single nucleotide polymorphisms by artificial mismatch hybridization," *Nature Biotechnology* 15:331–335 (1997).

Gupta, et al., "Expression of HIV–1 RNA in plasma correlates with the development of AIDS: A multicenter AIDS cohort study," *Ninth International Conference on AIDS/Fourth STD World Congress* Jun. 6–11, 1993, Berlin, Germany.

Hacia, et al., "Detection of heterozygous mutations in BRCA1 using high density oligonucleotide arrays and two–color fluorescence analysis," *Nature Genetics* 14:441–447.

Haff & Smirnov, "Single–nucleotide polymorphism identification assays using a thermostable DNA polymerase and delayed extraction MALDI–TOF mass spectrometry," *Genome Res.* 7(4):378–88 (1997).

Hagiwara, et al., "Quantitation of hepatitis C Virus RNA in Serum of Asymptomatic Blood Donors and Patients with Type C Chronic Liver Disease," *Hepatology* 17(4):545–550 (1993).

Hanvey, et al., "Antisense and Antigene Properties of Peptide Nucleic Acids," *Science* 258: 1481–1485 (1992).

Hata, et al., "Structure of the Human Ornithine Transcarbamylase Gene," *J. Biochem.* 103: 302–308 (1988).

Hendrickson, et al., "High sensitivity multianalyte immunoassay using covalent DNA–labeled antibodies and polymerase chain reaction," *Nucleic Acids Res.* 23(3):522–529 (1995).

Hermanson, et al., eds., *Immobilized Affinity Ligands,* (Academic Press, New York, 1992).

Holloway, et al., "An exonuclease–amplification coupled capture technique improves detection of PCR product," *Nucleic Acids Research* 21:3905–3906 (1993).

Hoy, et al., "Bromodeoxyuridine/DNA analysis of replication in CHO cells after exposure to UV light," *Mutation Research* 290:217–230 (1993).

Hsuih, et al., "Quantitative Detection of HCV RNA Using Novel Ligation–Dependent Polymerase Chain Reaction", *American Association for the Study of Liver Diseases,* (Chicago, IL, Nov. 3–7, 1995) [poster abstract].

Itakura, et al., "Synthesis and Use of Synthetic Oligonucleotides," *Annual Review of Biochemistry* 53:323–356 (1984).

Jacobsen, et al., "The N–Terminal Amino–Acid Sequences of DNA Polymerase I from *Escherichia coli* and of the Large and the Small Fragments Obtained by a Limited Proteolysis," *Eur. J. Biochem.* 45:623–627 (1974).

Jalanko, et al., "Screening for defined cystic fibrosis mutations by solid–phase minisequencing," *Clin Chem.* 38(1):39–43 (1992).

Jiang, et al., "An efficient method for generation and subcloning of tandemly repeated DNA sequences with defined length, orientation and spacing," *Nucl. Acids Res.* 24:3278–3279 (1996).

Johnstone & Thorpe, *Immunochemistry In Practice* (Blackwell Scientific Publications, Oxford, England, 1987) pp. 209–216 and 241–242.

Jónsson, et al., "Sequence of the DNA ligase–encoding gene from *Thermus scotoductus* and conserved motifs in DNA ligases," *Gene* 151(1&2):177–180 (1995).

Jung, et al., "Bacteriophage PRDI DNA polymerase: Evolution of DNA polymerases," *Proc. Natl. Acad. Sci. USA* 84:8287 (1987).

Kaboord & Benkovic, "Accessory proteins function as matchmakers in the assembly of the T4 DNA polymerase holoenzyme," *Current Biology* 5: 149–157 (1995).

Kälin, et al., "Evaluation of the ligase chain reaction (LCR) for the detection of point mutations," *Mutation Research* 283(2): 119–123 (1992).

Kaplan, et al., "Rapid photolytic release of adenosine 5'-triphosphate from a protected analogue: utilization by the Na:K pump of human red blood cell ghosts" *Biochem.* 17:1929–1935 (1978).

Kellogg, et al., "TaqStart Antibody™: "Hot Start" PCR Facilitated by a Neutralizing Monoclonal Antibody Directed Against Taq DNA Polymerase," *Bio Techniques* 16(6):1134–1137 (1994).

Kerkhof, "A Comparison of Substrates for Quantifying the Signal from a Nonradiolabeled DNA Probe," *Analytical Biochemistry* 205:359–364 (1992).

Khrapko, et al., "Hybridization of DNA with Oligonucleotides Immobilized in Gel: A Convenient Method for Detecting Single Base Substitutions," *Molecular Biology (Mosk) (USSR)* 25:718–730 (1991).

King, et al., "Bridging the Gap," *Journal of Biological Chemistry* 269(18):13061–13064 (1994).

Kobayashi et al., "Fluorescence–based DNA minisequence analysis for detection of known single–base changes in genomic DNA," *Mol Cell Probes.* 9(3):175–82 (1995).

Kong, et al., "Characterization of a DNA Polymerase from the Hyperthermophile Archaea *Thermococcus litoralis*," *Journal of Biological Chemistry* 268:1965–1975 (1993).

Kool, et al., "Circular oligonucleotides: New concepts in oligonucleotide design," *Annu. Rev. Biophys. Biomol. Struct.* 25:1–28 (1996).

Kunkel, et al., "Rapid and Efficient Site–Specific Mutagenesis without Phenotypic Selection," *Methods in Enzymology* 154: 367–382 (1987).

Lamture, et al., "Direct detection of nucleic acid hybridization on the surface of a charge coupled device," *Nucl. Acids Res.* 22:2121–25 (1994).

Landegren, "Molecular mechanics of nucleic acid sequence amplification," *Trends Genetics* 9:199–202 (1993).

Landegren, et al., "A Ligase–Mediated Gene Detection Technique," *Science* 241:1077–1080 (1988).

Langer, et al., "Enzymatic synthesis of biotin–labeled polynucleotides: Novel nucleic acid affinity probes", *Proc. Natl. Acad. Sci. USA* 78(11):6633–6637 (1981).

Lawyer, et al., "High–level Expression, Purification, and Enzymatic Characterization of Full–length *Thermus aquaticus* DNA Polymerase and a Truncated Form Deficient in 5' to 3' Exonuclease Activity," *PCR Methods Applications* 2(4):275–287 (1993).

Lefrere, et al., "Towards a new predictor of AIDS progression through the quantitation of HIV–1 DNA copies by PCR in HIV–infected individuals," *British Journal of Haematology* 82(2): 467–471 (1992).

Lesnik & Freier, "Relative Thermodynamic Stability of DNA, RNA, and DNA:RNA Hybrid Duplexes: Relationship with Base Composition and Structure,"*Biochemistry* 34: 10807–10815 (1995).

Liu, et al., "Rolling circle DNA synthesis: Small circular oligonucleotides as efficient templates for DNA polymerases," *J. Am. Chem. Soc.* 118:1587–1594 (1996).

Lizardi, et al., "Cascade rolling circle amplification, a homogeneous fluorescence detection system for DNA diagnostics," *Clin. Chem.* 43: 2219–20 (1997).

Lizardi, et al., "Mutation detection and single–molecule counting using isothermal rolling–circle amplification," *Nat Genet.* 19(3):225–32 (1998).

Lockhart, et al., "Expression monitoring by hybridization to high–density oligonucleotide arrays," *Nature Biotechnology* 14:1675–1680 (1996).

Lu, et al., "High Concentration of Peripheral Blood Mononuclear Cells Harboring Infectious Virus Correlates with Rapid Progression of Human Immunodeficiency Virus Type 1–Related Diseases," *JID* 168(5):1165–8116 (1993).

Lukyanov, et al., "Molecule by molecule PCR amplification of complex DNA mixtures for direct sequencing: an approach to in vitro cloning," *Nucleic Acids Res.* 24(11):2194–5 (1996).

Luo, et al., "Improving the fidelity of *Thermus thermophilus* DNA ligase," *Nucl. Acids Res.* 24:3071–3078 (1996).

Marshall, et al., "Detection of HCV RNA by the asymmetric gap ligase chain reaction," *PCR Methods Appl.* 4(2):80–4 (1994).

Maskos & Southern, "Oligonucleotide hybridizations on glass supports: a novel linker for oligonucleotides synthesized in situ," *Nucleic Acids Research* 20:1679–1684 (1992).

Matsumoto, et al., "Primary structure of bacteriophage M2 DNA polymerase: conserved segments within protein–priming DNA polymerases and DNA polymerase I of *Escherichia coli*," *Gene* 84(2): 247–255 (1989).

McCray, et al., "A new approach to time–resolved studies of ATP–requiring biological systems: Laser flash photolysis of caged ATP," *Proc. Natl. Acad. Sci. USA* 77:7237–7241 (1980).

McGraw, et al., "Sequence–dependant oligonucleotide–target duplex stabilities: rules from empirical studies with a set of twenty–mers," *Biotechniques* 8:674–678 (1990).

Melton, et al., "Efficient in vitro synthesis of biologically active RNA and RNA hybridization probes from plasmids containing a bacteriophage SP6 promoter," *Nucleic Acids Res.* 12(18):7035–56 (1984).

Metzker, et al., "Termination of DNA synthesis by novel 3'-modified-deoxyribonucleotide 5'-triphosphates" *Nucleic Acids Research* 22:4259–4267 (1994).

Moretti, et al., "Enhancement of PCR amplification yield and specificity using AmpliTaq Gold DNA polymerase," *Biotechniques.* 25(4):716–22 (1998).

Mujumdar, et al., "Cyanine dye labeling reagents containing isothiocyanate groups" *Cytometry* 10:11–19 (1989).

Narang, et al., "Chemical Synthesis of Deoxyoligonucleotides by the Modified Triester Method", *Methods Enzymology* 65:610–620 (1980).

Newton, et al., "Analysis of any point mutation in DNA. The amplification refractory mutation system (ARMS)," *Nucleic Acids Res.* 17(7):2503–16 (1989).

Nielsen, et al., "Peptide Nucleic Acid (PNA). A DNA Mimic with a Peptide Backbone," *Bioconjugate Chemistry,* 5: 3–7 (1994).

Nielsen, et al., "Peptide nucleic acids (PNAs): Potential anti–sense and anti–gene agents," *Anti–Cancer Drug Design,* 8: 53–63 (1993).

Nikiforov, et al., "The Use of Phosphorothioate Primers and Exonuclease Hydrolysis for the Preparation of Single–stranded PCR Products and their Detection by Solid–phase Hybridization," *PCR Methods and Applications* 3: 285–291 (1994).

Nikiforov, et al., "Genetic Bit Analysis: a solid phase method for typing single nucleotide polymorphisms," *Nucleic Acids Res.* 22(20):4167–75 (1994).

Nilsson, et al., "Padlock Probes: Circularizing Oligonucleotides for Localized DNA Detection," *Science* 265: 2085–2088 (1994).

Nilsson, et al., "Padlock probes reveal single–nucleotide differences, parent of origin and in situ distribution of centromeric sequences in human chromosomes 13 and 21," *Nat Genet.* 16(3):252–5 (1997).

Ørum, et al., "Single base pair mutation analysis by PNA directed PCR clamping," *Nucleic Acids Research* 21(23):5332–5336 (1993).

Panasenko, et al., "A Simple, Three–Step Procedure for the Large Scale Purification of DNA Ligase from a Hybrid λ Lysogen Construction in Vitro," *Journal Biological Chemistry* 253:4590–4592 (1978).

Parker, et al., "Targeted gene walking polymerase chain reaction," *Nucl. Acids Res.* 19:3055–60 (1991).

Pease, et al., "Light–generated oligonucleotide arrays for rapid DNA sequence analysis," *Proc. Natl. Acad. Sci. USA* 91(11):5022–5026 (1994).

Piatak, et al., "High Levels of HIV–1 in Plasma During All Stages of Infection Determined by Competitive PCR," *Science* 259(5102):1749–1754 (1993).

Pillai, et al., "Photoremovable protecting groups in organic synthesis," *Synthesis* 1–26 (1980).

Pokrovskaya & Gurevich, "In vitro transcription: preparative RNA yields in analytical scale reactions," *Anal Biochem.* 220(2):420–3 (1994).

Prakash & Kool, "Structural effects in the recognition of DNA by circular oligonucleotides," *J. Amer. Chem. Soc.* 114:3523–3527 (1992).

Ramsing, et al., "Helix–coil transition of parallel–stranded DNA. Thermodynamics of hairpin and linear duplex oligonucleotides," *Biochem.* 28:9528–9535 (1989).

Richards, et al., "Conditional mutator phenotypes in hMS2H2–deficient tumor cell lines," *Science* 277:1523–1526 (1997).

Ried, et al., "Simultaneous visualization of seven different DNA probes by in situ hybridization using combinatorial fluorescence and digital imaging microscopy," *Proc Natl Acad Sci U S A.* 89(4):1388–92 (1992).

Rigler & Romano, "Differences in the Mechanism of Stimulation of T7 DNA Polymerase by Two Binding Modes of *Escherichia coli* Single–stranded DNA–binding Protein," *Journal of Biological Chemistry,* 270(15): 8910–8919 (1995).

Rychlik, et al., "Optimization of the annealing temperature for DNA amplification in vitro," *Nucleic Acids Research* 18(21): 6409–6412 (1990).

Rys & Persing, "Preventing false positives: quantitative evaluation of three protocols for inactivation of polymerase chain reaction amplification products," *J Clin Microbiol.* 31(9):2356–60 (1993).

Saksela, et al., "Human immunodeficiency virus type 1 mRNA expression in peripheral blood cells predicts disease progression independently of the numbers of CD4+ lymphocytes," *Proc. Natl. Acad. Sci. USA* 91(3): 1104–1108 (1994).

Sambrook, et al., "Molecular Cloning: A Laboratory Manual, Second Edition" (Cold Spring Harbor Laboratory Press, Cold Spring Harbor, N.Y., 1989 (Chapters 5, 6)).

Saris, et al., "Blotting of RNA onto ion exchange paper allowing subsequent characterization by in situ translation in addition to blot hybridization," *Nucleic Acids Res.* 10(16):4831–43 (1982).

Schena, et al., "Quantitative Monitoring of Gene Expression Patterns with a Complementary DNA Microarray," *Science* 270:467–470 (1995).

Schena, et al., "Parallel human genome analysis: Microarray–based expression monitoring of 1000 genes," *Proc. Natl. Acad. Sci. USA* 91:10614–10619 (1994).

Schenborn & Meirendorf, "A novel transcription property of SP6 and 17 RNA polymerase: dependence on template structure," *Nucleic Acids Research* 13(17):6223–6236 (1985).

Schwarz, et al., "Improved yields of long PCR products using gene 32 protein," *Nucl. Acid Res.* 18:1079 (1989).

Siegal, et al., "A Novel DNA Helicase from Calf Thymus," *Journal of Biological Chemistry* 267(19): 13629–13635 (1992).

Skaliter & Lehman, "Rolling circle DNA replication in vitro by a complex of herpes simplex virus type 1–encoded enzymes," *Proc. Natl. Acad. Sci. USA* 91(22):10665–10669 (1994).

Speicher, et al., "Karyotyping human chromosomes by combinatorial multi–fluor FISH," *Nature Genetics* 12(4): 368–375 (1996).

Stimpson, et al., "Real–time detection of DNA hybridization and melting on oligonucleotide arrays by using optical wave guides," *Proc. Natl. Acad. Sci. USA* 92(14):6379–6383 (1995).

Strauss & Jacobowitz, "Quantitative measurement of calretinin and beta–actin mRNA [correction of mRNAIN] in rat brain micropunches without prior isolation of RNA," *Mol Brain Res.* 20(3):229–39 (1993).

Studier, et al., "Use of T7 RNA Polymerase to Direct Expression of Cloned Genes," *Methods in Enzymology* 185: 60–89 (1990).

Syvänen, et al., "Fast quantification of nucleic acid hybrids by affinity–based hybrid collection," *Nucleic Acids Res.* 14(12):5037–48 (1986).

Tabor & Richardson, "Selective inactivation of the exonuclease activity of bacteriophage T7 DNA polymerase by in vitro mutagenesis," *J. Biol. Chem.* 264:6447–6458 (1989).

Tabor & Richardson, "Selective oxidation of the exonuclease domain of bacteriophage T7 DNA polymerase," *J. Biol. Chem.* 262:15330–15333 (1987).

Taylor, ed, *Protein immobilization: fundamentals and applications* (M. Dekker, New York, 1991).

Tsurumi, et al., "Functional Interaction between EpsteinBarr Virus DNA Polymerase Catalytic Subunit and Its Accessory Subunit In Vitro," *Journal of Virology* 67(12):7648–7653 (1993).

Tyagi & Kramer, "Molecular beacons: probes that fluoresce upon hybridization," *Nature Biotechnology* 14:303–308 (1996).

Velculescu, et al., "Serial analysis of gene expression," *Science.* 270(5235):484–7 (1995).

Vogelstein, et al., "Supercoiled loops and eucaryotic DNA replicaton," *Cell.* 22(1 Pt 1):79–85 (1980).

Waggoner, "Covalent labeling of proteins and nucleic acids with fluorophores," *Meth. Enzymology* 246:362–373 (1995).

Walker, et al., "Strand displacement amplification—an isothermal, in vitro DNA amplification technique," *Nucleic Acids Res.* 20(7):1691–6 (1992).

Walter & Strunk, "Strand displacement amplification as an in vitro model for rolling–circle replication: deletion formation and evolution during serial transfer," *Proc Natl Acad Sci U S A.* 91(17):7937–41 (1994).

Wansink, et al., "Fluorescent Labeling of Nascent RNA Reveals Transcription by RNA Polymerase II in Domains Scattered Throughout the Nucleus," *Journal of Cell Biology* 122(2): 283–293 (1993).

Welford, et al., "Detection of differentially expressed genes in primary tumor tissues using representational differences analysis coupled to microarray hybridization," *Nucleic Acids Res.* 26(12):3059–65 (1998).

Wiedmann, et al., "Ligase Chain Reaction (LCR)—Overview and Applications," *PCR Methods and Applications* (Cold Spring Harbor Laboratory Press, Cold Spring Harbor Laboratory, NY, 1994) pp. S51–S64.

Winn–Deen, et al., "Non–radioactive detection of Mycobacterium tuberculosis LCR products in a microtitre plate format," *Molecular and Cellular Probes* (England) 7(3):179–186 (1993).

Yang, et al., "Combining SSH and cDNA microarrays for rapid identification of differentially expressed genes," *Nucleic Acids Res.* 27(6):1517–23 (1999).

Young & Anderson, "Quantitative analysis of solution hybridisation," *Nucleic Acid Hybridisation: A Practical Approach* pp. 47–71 (IRL Press, 1985).

Yu, et al., "Cyanine dye dUTP analogs for enzymatic labeling of DNA probes," *Nucleic Acids Research* 22(15): 3226–3232 (1994).

Zehavi, et al., "Light sensitive glycosides. I. 6–Nitoveratryl $\beta$–D–Glucopyranoside and 2–Nitrobenzyl $\beta$–D–Glucopyranoside," *J. Organic Chem.* 37:2281–2288 (1972).

Zhu & Ito, "Purification and characterization of PRD1 DNA polymerase," *Biochimica Biophysica Acta* 1219(2): 267–276 (1994).

Zijderveld & Van Der Vliet, "Helix–Destabilizing Properties of the Adenovirus DNA–Binding Protein," *Journal of Virology* 68(2):1158–1164 (1994).

* cited by examiner

LINEAR VECTORS  CIRCULAR VECTORS 1, 2, 3 ARE RESTRICTION SITES 5, 6 ARE STICKY ENDS COMPATIBLE WITH 1 AND 2

4 IS BIOTIN OR ANY HAPTEN

DIGESTED PCR PRODUCT LIGATED TO ADAPTOR

MOLECULAR CLONING USING ROLLING CIRCLE AMPLIFICATION

CROSS-REFERENCE TO RELATED APPLICATIONS

This application claims benefit of U.S. Provisional Application Ser. No. 60/100,327, filed Sep. 15, 1998. Application Ser. No. 60/100,327, filed Sep. 15, 1998, is hereby incorporated herein by reference.

BACKGROUND OF THE INVENTION

The disclosed invention is generally in the field of molecular cloning and nucleic acid amplification, and specifically involves rolling circle replication of nucleic acid molecules inserted into circular vectors.

DNA molecular cloning is routinely carried out using plasmid, phage, or viral vectors that replicate inside cells. A method, in which individual DNA molecules are cloned in solution by serial dilution and subsequent PCR amplification from tubes containing single molecules has been described (Lukyanov et al., *Nucleic Acid Research* 24:2194–2195 (1996)). A method has also been described for cloning RNA populations derived from single RNA molecules in an immobilized medium (Chetverina and Chetverin, *Nucleic Acids Research* 21:2349–2353 (1993)). While both of these methods allow in vitro cloning, neither is practical for high throughput cloning.

Velculescu et al., *Science* 270:484–487 (1995), have described a method for the quantitative cataloguing and comparison of expressed genes in normal, developmental, and disease states. The method, termed serial analysis of gene expression (SAGE), is based in the use of relatively short sequence tags for the unique identification of cDNAs derived from mRNA transcripts. While this method is very powerful, the study of low-abundance mRNAs can require several months of work in order to obtain sufficient sequence information for a complete SAGE analysis of one tissue sample. Thus, there is a need for a method to obtain the sequence of sequence tags more rapidly.

It is therefore an object of the present invention to provide a more efficient method of in vitro molecular cloning.

It is also an object of the present invention to provide vectors and kits useful for in vitro cloning.

It is also an object of the present invention to provide an automated method molecular cloning.

It is also an object of the present invention to provide a more efficient method of sequential analysis of gene expression.

BRIEF SUMMARY OF THE INVENTION

Disclosed are reagents and a method for efficient in vitro molecular cloning of nucleic acid molecules of interest. Because the method is entirely in vitro, it can be automated and scaled-up in ways that are not possible in cell-based molecular cloning. The method involves insertion of a nucleic acid molecule of interest in a linear vector to form a circular vector where one strand is continuous and the other strand is discontinuous. The continuous strand of the circular vector is then amplified by rolling circle replication, amplifying the inserted nucleic acid molecule in the process. The amplification is rapid and efficient since it involves a single, isothermic reaction that replicates the vector sequences exponentially. The amplification process is amenable to automation where multiple reactions are carried out simultaneously in a small area. The amplified nucleic acid can be used for any purpose and in any manner that nucleic acid cloned or amplified by known methods can be used. This includes sequencing, probing, restriction analysis, subcloning, transcription, hybridization or denaturation analysis, further amplified, and storage for future use or analysis.

The insertion reaction involves insertion of a double-stranded nucleic acid molecule into a double-stranded linear vector to produce a double-stranded circular vector. The use of circular vectors facilitates the selection of molecules that have successfully incorporated inserts. The amplification reaction involves rolling circle replication of a single-stranded circular nucleic acid molecule.

A key feature of the method, which facilitates double-stranded insertion followed by single-stranded amplification, is formation of the circular vector in such a way that one of its strands is a closed circular strand (that is, continuous) while the other strand is not a closed circular strand (that is, it has a nick, a gap, an overlap, or is otherwise discontinuous). This feature is most useful, and most effectively accomplished, when, by operation of the method, the closed strand and the open strand are predetermined; that is, when a particular strand of the vector is selectively left discontinuous.

With rolling circle replication, amplification takes place not in cycles, but in a continuous, isothermal replication. This makes amplification less complicated and much more consistent in output. A single round of rolling circle replication results in a large amplification of the circular vector, orders of magnitude greater than a single cycle of PCR replication and other amplification techniques in which each cycle is limited to a doubling of the number of copies of a target sequence.

Following amplification, the amplified nucleic acid can be used for any purpose. Numerous methods for the use and manipulation of cloned or isolated nucleic acid are known and can be applied to nucleic acid amplified in the present method. For example, the nucleic acid can be sequenced, probed, subjected to restriction analysis, subcloned, transcribed, subjected to hybridization or denaturation analysis, further amplified, or stored. Diagnostic methods, such as sequencing and probing for specific sequences, are preferred.

Libraries of cloned nucleic acids formed by the disclosed method can be screened using any of the methods used for screening conventional libraries. For example, cDNA libraries made using the disclosed method can be analyzed using conventional screens. Libraries can also be used for in situ transcription to generate RNA colonies, which can then be analyzed (in situ or in replicas) by appropriate screens, such as aptamer screens or ribozyme activity screens. Libraries can also be screened by in situ translation on array replicas (see, for example, Saris et al., *Nucleic Acids Res.* 10:4831–4843 (1982)). Libraries can also be screened by in situ coupled transcription-translation systems, and subsequent catalytic activity assays for the analysis of mutagenized enzymes. Libraries can be screened and cataloged by sequencing and use of the data for the analysis of cDNA abundancies, which is useful for RNA profiling and serial analysis of gene expression (SAGE; Velculescu et al., *Science* 270:484–487 (1995)).

DETAILED DESCRIPTION OF THE INVENTION

Figure 1A:
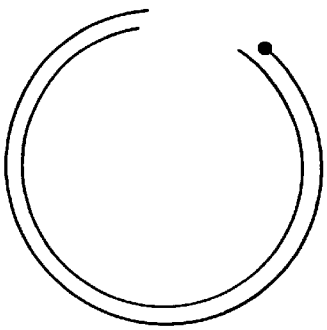
FIGS. 1A–1C are diagrams of examples of various forms of linear vectors and the circular vectors, having one continuous strand and one discontinuous strand, that result upon insertion of a nucleic acid molecule.
Figure 1A:
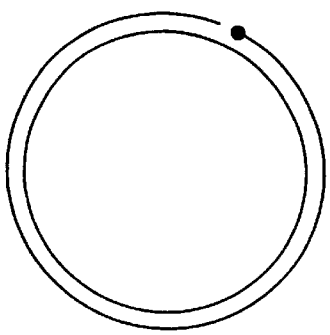
Figure 1A:
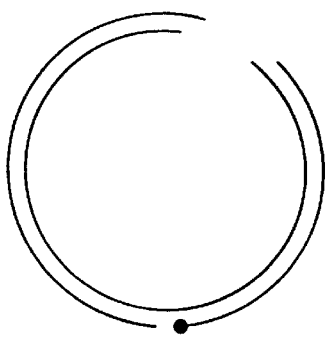
Figure 1A:
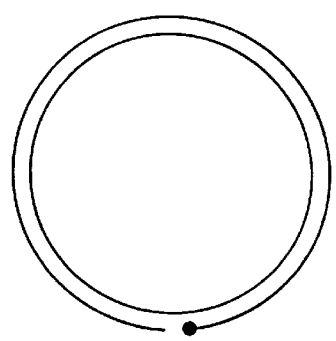
Figure 1A:
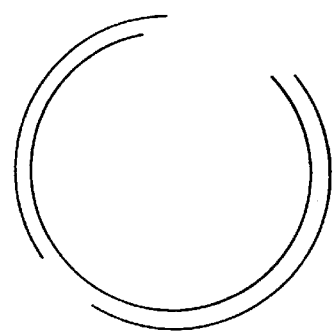
Figure 1A:
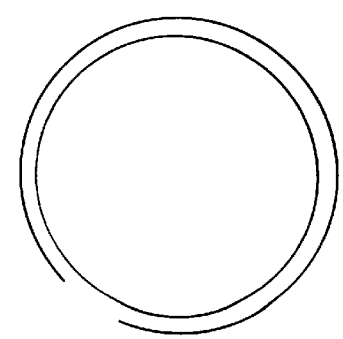

Disclosed are reagents and a method for efficient in vitro molecular cloning of nucleic acid molecules of interest. Because the method is entirely in vitro, it can be automated and scaled-up in ways that are not possible in cell-based molecular cloning. The method involves insertion of a nucleic acid molecule of interest in a linear vector to form a circular vector where one strand is continuous and the other strand is discontinuous. The continuous strand of the circular vector is then amplified by rolling circle replication, amplifying the inserted nucleic acid molecule in the process. The amplification is rapid and efficient since it involves a single, isothermic reaction that replicates the vector sequences exponentially. The amplification process is amenable to automation where multiple reactions are carried out simultaneously in a small area. The amplified nucleic acid can be used for any purpose and in any manner that nucleic acid cloned or amplified by known methods can be used. This includes sequencing, probing, restriction analysis, subcloning, transcription, hybridization or denaturation analysis, further amplified, and storage for future use or analysis.

The insertion reaction involves insertion of a double-stranded nucleic acid molecule into a double-stranded linear vector to produce a double-stranded circular vector. The use of circular vectors facilitates the selection of molecules that have successfully incorporated inserts. The amplification reaction involves rolling circle replication of a single-stranded circular nucleic acid molecule. In its most useful forms, the disclosed method involves insertion of nucleic acid molecules of interest into a vector and separate amplification of the resulting recombinant vectors to produce separate nucleic acid "colonies," each representing a clonal population of nucleic acid sequences present in founding vector of that "colony."

A key feature of the method, which facilitates double-stranded insertion followed by single-stranded amplification, is formation of the circular vector in such a way that one of its strands is a closed circular strand (that is, continuous) while the other strand is not a closed circular strand (that is, it has a nick, a gap, an overlap, or is otherwise discontinuous). This feature is most useful, and most effectively accomplished, when, by operation of the method, the closed strand and the open strand are predetermined; that is, when a particular strand of the vector is selectively left discontinuous.

With rolling circle replication, amplification takes place not in cycles, but in a continuous, isothermal replication. This makes amplification less complicated and much more consistent in output. A single round of rolling circle replication results in a large amplification of the circular vector, orders of magnitude greater than a single cycle of PCR replication and other amplification techniques in which each cycle is limited to a doubling of the number of copies of a target sequence.

The present method is an alternative to traditional molecular cloning involving clonal amplification in cells harnessing the natural nucleic acid replication in, and growth and division of, the cells. The present method has several advantages over this traditional method. First, it is much more rapid. Traditional molecular cloning usually requires at least twelve hours of cell growth in the best cell-based cloning methods to produce a million copies of a single vector. In contrast, the present method allows production of millions or billions of copies of a single vector in only 60 to 90 minutes.

Once a clonal culture or colony of cells is grown, there is still the problem of separating the amplified nucleic acid from the cell and all the cellular components. Although numerous methods have been devised over the years for such purification, they remain both time consuming and ineffective (that is, cellular contaminants remain with the isolated nucleic acid). Generally, the amount of time for the purification and the level of purity obtain from nucleic acid isolation methods is proportional: more time, more purity; less time, less purity. In contrast, the present method accomplishes clonal amplification in an uncomplicated mix of just a few well-defined components: the vector, one or two types of primers, nucleotides, and polymerase. The purification of the amplified nucleic acid is correspondingly simplified. Most significantly, the amplification reaction in present method need not result in a complex mixture of nucleic acids as is true of cell-based molecular cloning.

The present method also has advantages over cyclic amplification methods such as the polymerase chain reaction (PCR). Rolling circle replication is more rapid and has higher yields than PCR. Significantly, the products of rolling circle replication are tandemly repeated amplicons of double-stranded DNA. These amplicons, if carried as contaminants to any surface or vessel, are unable to seed new rolling circle replication reactions. In other words, the amplified DNA is non-contaminating because it is a replication dead-end. By contrast, PCR or SDA amplicons are potentially contaminating.

Following amplification, the amplified nucleic acid can be used for any purpose. Numerous methods for the use and manipulation of cloned or isolated nucleic acid are known and can be applied to nucleic acid amplified in the present method. For example, the nucleic acid can be sequenced, probed, subjected to restriction analysis, subcloned, transcribed, subjected to hybridization or denaturation analysis, fuirther amplified, or stored. Diagnostic methods, such as sequencing and probing for specific sequences, are preferred.

The nucleotide sequence of the amplified sequences can be determined either by conventional means or by primer extension sequencing of amplified target sequence. One preferred form of sequencing for use with amplified sequences produced with the disclosed method is nanosequencing or single-nucleotide extension sequencing. Nanosequencing methods are described below and by Jalanko el al., *Clinical Chemistry* 38:39–43 (1992); Nikiforov et al., *Nucleic Acids Research* 22:4167–4175 (1994); and Kobayashi et al., *Molecular and Cellular Probes* 9:175–182 (1995).

Two forms of sequencing that can be used with the disclosed method are described in PCT Application WO 97/20948. One is single nucleotide primer extension sequencing involving interrogation of a single nucleotide in an amplified target sequence by incorporation of a specific and identifiable nucleotide based on the identity of the interrogated nucleotide. The other is degenerate probe primer extension sequencing involving sequential addition of degenerate probes to an interrogation primer hybridized to amplified target sequences.

Libraries of cloned nucleic acids formed by the disclosed method can be screened using any of the methods used for screening conventional libraries. For example, cDNA libraries made using the disclosed method can be analyzed using conventional screens. Libraries can also be used for in situ transcription to generate RNA colonies, which can then be analyzed (in situ or in replicas) by appropriate screens, such as aptamer screens or ribozyme activity screens. Libraries can also be screened by in situ translation on array replicas (see, for example, Saris et al., *Nucleic Acids Res.* 10:4831–4843 (1982)). Libraries can also be screened by in situ coupled transcription-translation systems, and subsequent catalytic activity assays for the analysis of mutagenized enzymes. Libraries can be screened and cataloged by sequencing and use of the data for the analysis of cDNA abundancies, which is useful for RNA profiling and serial analysis of gene expression (SAGE; Velculescu et al., *Science* 270:484–487 (1995)).

One embodiment of the disclosed method is a method of isolating and amplifying a nucleic acid molecule, where the method involves:

(a) ligating a nucleic acid molecule into a linear vector to form a circular vector including the vector and the nucleic acid molecule, where the linear vector is a double-stranded linear nucleic acid including two nucleic acid strands, where the second strand of the circular vector is discontinuous, and where the first strand in the circular vector is a closed circular strand, and (b) amplifying the first strand by rolling circle replication to form tandem sequence DNA, where the amplification results in amplification of the nucleic acid molecule in the first strand.

The method can be practiced and expanded in several ways. For example, the second strand of the linear vector can contain at least one nick, where the nick cannot be ligated. The linear vector can be designed such that either the 5' or the 3' end of the second strand of the linear vector cannot be ligated. The linear vector can be designed such that the second strand of the linear vector contains at least one gap or overlap. The method can be extended to include, following ligation and prior to amplification, separation of the first strand from the second strand. The second strand of the vector can include an affinity tag. In this case, the first strand can be separated from the second strand by binding the affinity tag to a substrate, denaturing the first and second strands prior to, simultaneous with, or following binding, and separating the first strand from the substrate.

The second strand of the linear vector can also be designed to contain at least one overlap, where part of the overlapping portions of the second strand are complementary, and where the 3' end of the overlap extends beyond the part of the overlapping portions that are complementary. In this case, the first strand can be separated from the second strand by ligating one end of the second strand to a nucleic acid molecule coupled to a substrate, denaturing the first and second strands following ligation of the second strand, and separating the first strand from the substrate.

The method can also be practiced such that step (a) involves ligating a plurality of nucleic acid molecules into a plurality of linear vectors in a single reaction to form a plurality of circular vectors, each circular vector containing at least one nick, gap, or overlap in the second strand, such that step (b) involves amplifying the first strand of the plurality of circular vectors, and such that, prior to amplification, the ligation reaction is divided to produce a plurality of separate amplification reactions. The method can be extended to include making a replica of the amplification reactions. The replica of the amplification reactions can be made by contacting the amplification reactions with a surface to which nucleic acids can bind. The replica of the amplification reactions can also be made by transferring part of each amplification reaction to form a replica amplification reaction.

In the method, the ligation reaction can be divided by spreading the ligation reaction onto a surface to form a spread, where the separate amplification reactions are the locations of circular vectors on the surface after spreading. In this case, a replica of the amplification reactions can be made by contacting the spread with a second surface to which nucleic acids can bind.

Any number or all of the amplification reactions can be ordered as an array of reaction droplets or in an array of reaction vessels. In this case, following amplification, all or part of the contents of any number or all the individual reaction droplets or reaction vessels are transferred by one to one mapping to a new set of reaction droplets or reaction vessels.

The method can be further extended by, following amplification, determining the presence of amplified nucleic acid in the amplification reactions, and transferring all or a part of the contents of the amplification reactions containing amplified nucleic acid reaction to a new set of reaction droplets or reaction vessels.

Replicas of the amplification reactions can be made by contacting the amplification reactions with a surface treated with an affinity target capable of binding an affinity tag, where the amplified nucleic include affinity tags incorporated during amplification, such that a portion of each amplification reaction is transferred to the surface. The affinity tag is preferably biotin and the affinity target is preferably streptavidin. The affinity tag is also preferably a reactive moiety and the affinity target is preferably a corresponding reactive moiety, such that a chemical reaction between the affinity tag and the affinity target results in the amplified nucleic acid being covalently coupled to the surface. In this case, it is preferred that the affinity target is phenylene diisothiocyanate, disuccinimidylcarbonate, disuccinimidyloxolate or dimethylsuberimidate and the affinity tag is a reactive amine.

A replica of the amplification reactions can also be made by transferring part of each amplification reaction to form a replica amplification reaction. Following amplification, all or part of the contents of any number or all of the reaction droplets or reaction vessels can be transferred and combined to create one or more sets of pooled reactions. The amplification reactions can also be arranged on the surface of a substrate. Preferred substrates include acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfiunerate, collagen, glycosaminoglycans, polyamino acids, chemical resistant metals, or corrosion resistant metals.

The ligation reactions can also be diluted prior to division of the ligation reaction into amplification reactions such that, on average, each amplification reaction contains a single circular vector. A sample of each amplification reaction can also be collected. Nucleic acid molecules in the amplification reactions or in the collected samples can also be detected or sequenced.

In the disclosed method, rolling circle replication can be primed by the second strand on the circular vector or by a rolling circle replication primer. The tandem sequence DNA formed after amplification can itself be amplified by strand displacement replication to form secondary tandem sequence DNA. This secondary tandem sequence DNA can also be amplified by strand displacement replication to form tertiary tandem sequence DNA. Strand displacement replication of the tandem sequence can be primed by a strand displacement primer.

The method can also include detection of one or more amplified nucleic acid molecules in one or more of the amplification reactions. In a preferred embodiment, the nucleic acid molecules can be derived from cDNA generated by suppression subtractive hybridization. In another preferred embodiment, the plurality of nucleic acid molecules can be all derived from the same source.

Detection can be accomplished by, following amplification, creating a replica of the amplification reactions, contacting the amplification reactions with a first set of labeled nucleic acid probes and the replica amplification reactions with a second set of labeled nucleic acid probes, and comparing the pattern of hybridization of the first set of probes to the pattern of hybridization of the second set of probes, where differences in the patterns of hybridization indicate differences in the probe sets. Following detection amplification reactions that hybridize to the first set of probes but not to the second set of probes, amplification reactions that hybridize to the second set of probes but not to the first set of probes, amplification reactions that hybridize to the both sets of probes, or amplification reactions that do not hybridize to either set of probes can be selected for isolation or fuirther analysis.

Another embodiment of the disclosed method is an in vitro method of cloning nucleic acid molecules, where the method involves (a) dividing a nucleic acid sample to produce a plurality of separate amplification reactions, (b) amplifying nucleic acid molecules in the amplification reactions, (c) making a replica of the amplification reactions, (d) testing nucleic acid molecules in either the amplification reactions or the replica amplification reactions to identify nucleic acid molecules of interest, and (e) retrieving the identified nucleic acid molecules of interest from the corresponding amplification reactions or replica amplification reactions that were not tested.

In this embodiment, the nucleic acid sample can be divided by spreading the sample onto a surface to form a spread, such that the separate amplification reactions are the locations of circular vectors on the surface after spreading. The replica of the amplification reactions can be made by contacting the spread with a second surface to which nucleic acids can bind.

Another embodiment of the disclosed method is a method of isolating and amplifying nucleic acid molecules, where the method involves (a) ligating a plurality of nucleic acid molecules into a plurality of linear vectors in a single reaction to form a plurality of circular vectors, each circular vector including a vector and a nucleic acid molecule, where the linear vectors are double-stranded linear nucleic acid comprising two nucleic acid strands, where the circular vectors each contain at least one nick, gap, or overlap in the second strand, and where the first strand in each circular vector is a closed circular strand, (b) separating the first strands from the second strands, (c) diluting and dividing the first strands to produce a plurality of separate amplification reactions that, on average, each contain a single circular vector, (d) amplifying the first strands of the plurality of circular vectors by rolling circle replication to form tandem sequence DNA, where the amplification results in amplification of the nucleic acid molecules in the first strands.

The tandem sequence DNA formed after amplification can itself be amplified by strand displacement replication to form secondary tandem sequence DNA. This secondary tandem sequence DNA can also be amplified by strand displacement replication to form tertiary tandem sequence DNA.

Another embodiment of the disclosed method is a method of isolating and amplifying a nucleic acid molecule, where the method involves (a) ligating a nucleic acid molecule into a linear vector to form a circular vector comprising the vector and the nucleic acid molecule, where the linear vector is a double-stranded linear nucleic acid comprising two nucleic acid strands, where the circular vector contains at least one nick in the second strand, and where the first strand in the circular vector is a closed circular strand, (b) amplifying the first strand, where the amplification results in amplification of the nucleic acid molecule in the first strand.

Also disclosed is a kit for isolating and amplifying nucleic acid molecules, where the kit includes (a) a linear vector where the linear vector is a double-stranded linear nucleic acid comprising two nucleic acid strands, and where (1) the linear vector contains at least one nick, where the nick cannot be ligated, (2) either the 5' or the 3' end of the second strand of the linear vector cannot be ligated, (3) the second strand of the linear vector contains at least one gap, (4) the second strand of the linear vector contains at least one overlap, or (5) any combination of (1), (2), (3) or (4);

(b) a rolling circle replication primer, where the rolling circle replication primer is complementary to a portion of the first strand of the linear vector; and (c) a strand displacement primer, where the strand displacement primer matches a portion of the first strand of the linear vector.

Also disclosed is a linear vector where the linear vector is a double-stranded linear nucleic acid made up of two nucleic acid strands, where the second strand of the linear vector contains an affinity tag, and where (1) the linear vector contains at least one nick, where the nick cannot be ligated,
(2) either the 5' or the 3' end of the second strand of the linear vector cannot be ligated,
(3) the second strand of the linear vector contains at least one gap,
(4) the second strand of the linear vector contains at least one overlap, or
(5) any combination of (1), (2), (3) or (4).

Also disclosed is a linear vector where the linear vector is a double-stranded linear nucleic acid made up of two nucleic acid strands, where the second strand of the linear vector contains at least one overlap, part of the overlapping portions of the second strand are complementary, and the 3' end of the overlap extends beyond the part of the overlapping portions that are complementary.

I. Materials

The disclosed method makes use of linear vectors in which nucleic acid molecules of interest can be inserted to form circular vectors. The circular vectors contain one continuous strand and one discontinuous strand. The discontinuous strand may include an affinity tag which, by interaction with an affinity substrate, can facilitate separation of the continuous strand from the discontinuous strand. The continuous strand of the circular vector is amplified by rolling circle replication to form tandem sequence DNA (TS-DNA). Rolling circle replication is primed by a rolling circle replication primer complementary to a sequence in the continuous strand. The tandem sequence DNA itself may be amplified by strand displacement replication, to form secondary tandem sequence DNA, using strand displacement primers (complementary to a sequence in the tandem sequence DNA). The secondary tandem sequence DNA may also be amplified by strand displacement replication, to form tertiary tandem sequence DNA, using strand displacement primers or the rolling circle replication primers (complementary to a sequence in the secondary tandem sequence DNA). Multiple amplification reactions can be carried out in parallel, preferably in arrays or as spreads of diluted vectors on surfaces or embedded in agarose. The resulting "colonies" of amplified DNA represent molecular clones of the progenitor circular vectors with an inserted nucleic acid molecule. Collectively, such colonies form a library of cloned nucleic acid molecules that can be replica plated or arrayed, stored, and screened. These materials are described in detail below.

A. Nucleic Acid Molecules

The disclosed method can be used to clone or amplify any nucleic acid molecule of interest. The nucleic acid molecules can come from any source such as a cellular or tissue nucleic acid sample, a subclone of a previously cloned fragment, mRNA, chemically synthesized nucleic acid, genomic nucleic acid samples, nucleic acid molecules obtained from nucleic acid libraries, specific nucleic acid molecules, and mixtures of nucleic acid molecules. The disclosed method is particularly suited to producing libraries of cloned nucleic acid molecules starting with a complex mixture of nucleic acid molecules to be represented in the library. For example, cDNA can be produced from all of the mRNA in a cellular sample and used to make a cDNA library, or a library of genomic DNA can be produced from a genomic nucleic acid sample.

In the method, the nucleic acid molecule is inserted into a double-stranded linear vector. Preferably the insertion is accomplished by ligation, although any suitable coupling mechanism can also be used. Thus, the only requirement for nucleic acids molecules to be used in the disclosed method is that they can be coupled to the ends of a double-stranded nucleic acid molecule (that is, the linear vector). Single-stranded nucleic acid molecules, such as RNA, can be used by converting the molecule to be double-stranded. In the case of RNA molecules, this can be accomplished, for example, by producing a cDNA molecule of the RNA. Numerous methods are known for preparing and inserting nucleic acid molecules into vectors and any of these can be used to prepare nucleic acid molecules for use in the disclosed method (see, for example, Sambrook et al., *Molecular Cloning. A Laboratory Manual,* 2nd Edition (Cold Spring Harbor Laboratory Press, Cold Spring Harbor, N.Y., 1989)). Preferably, the nucleic acid molecule is prepared by generating sticky ends to facilitate insertion in the linear vector. This can be accomplished, for example by cleaving a nucleic acid molecule of interest, or a nucleic acid sample, with a restriction enzyme, or by adding linkers to the ends of nucleic acid molecules of interest that have, or can be processed to have sticky ends. One or both of the ends of the nucleic acid molecule can also be left blunt ended. The two ends of nucleic acid molecules to be used in the disclosed method can also be made different to allow directional insertion. For example, the to ends can have different sticky ends, or have one sticky end and one blunt end.

B. Linear Vectors

Linear vectors for use in the disclosed method are double-stranded nucleic acid molecules that can be circularized when its ends are coupled to a nucleic acid molecule. The characteristics of the linear vector are limited only by the requirements for the circular vector that results upon insertion of the nucleic acid molecule. Thus, the linear vector is designed such that, when the nucleic acid molecule is inserted and the linear vector is circularized, the resulting circular vector has one continuous, circular strand and one discontinuous strand.

The use of the term vector is not meant to indicate that the linear vector is required to have any characteristics beyond these, such as promoters, selectable markers, origins of replication, and other features present on traditional vectors for cloning in cells. However, the linear vector may contain these or any other features that do not interfere with the disclosed method. Such additional characteristics may be useful, for example, to allow transfer of the vector to cells to obtain expression, or to allow in vitro expression. Thus, the linear vector can be as simple as a short linker that facilitates circularization of a nucleic acid molecule of interest.

The linear vector is a double-stranded nucleic acid molecule where one of the strands will become part of the continuous strand of the circular vector and the other strand will become part of the discontinuous strand of the circular vector. For identification, the strand of the linear vector which will become part of the continuous strand of the circular vector is referred to as the first strand of the linear vector, and the strand of the linear vector which will become part of the discontinuous strand of the circular vector is referred to as the second strand of the linear vector. The first strand of a linear vector includes a sequence complementary to a rolling circle replication primer. This sequence is referred to as the primer complement portion of the linear vector. This facilitates amplification of the circular vector formed from the linear vector by rolling circle replication primed by the rolling circle replication primer. A separate primer complement portion is not required if the second strand of the circular vector is to serve as the rolling circle replication primer. It is preferred that the primer complement portion of the linear vector is near the 5' end of the first strand of the linear vector.

Figure 1B:
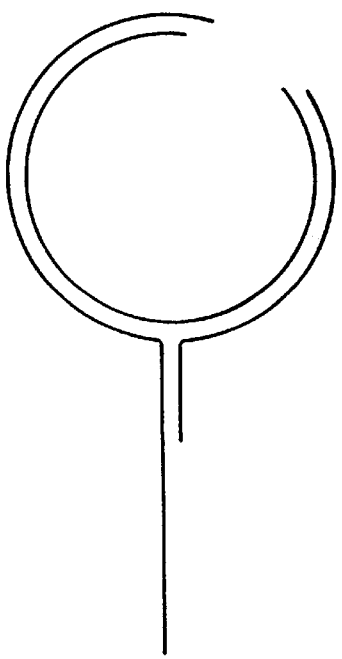
Figure 1B:
Figure 1B:
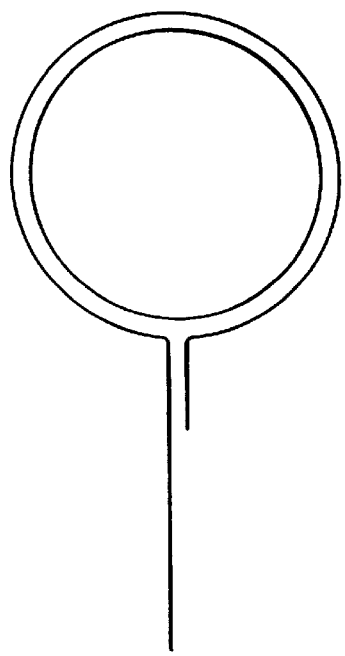
Figure 1B:
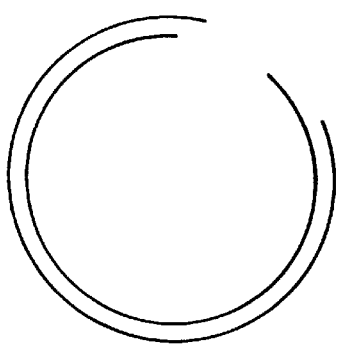
Figure 1B:
Figure 1B:
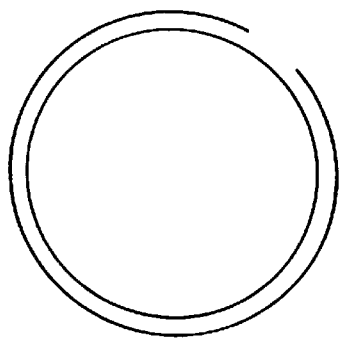
Figure 1B:
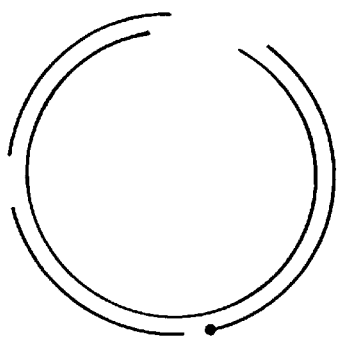
Figure 1B:
Figure 1B:
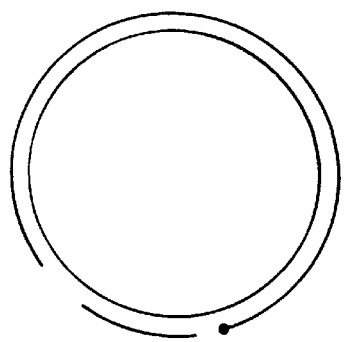
Figure 1C:
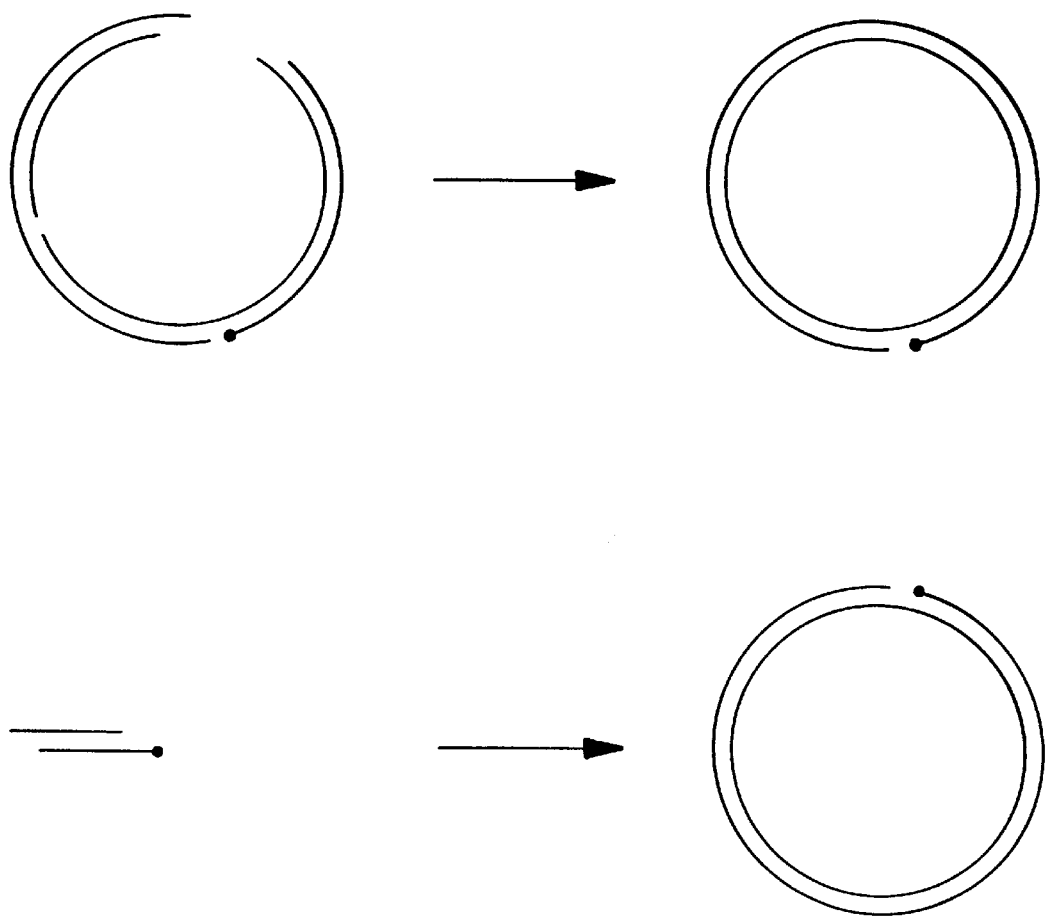
Figure 2A:
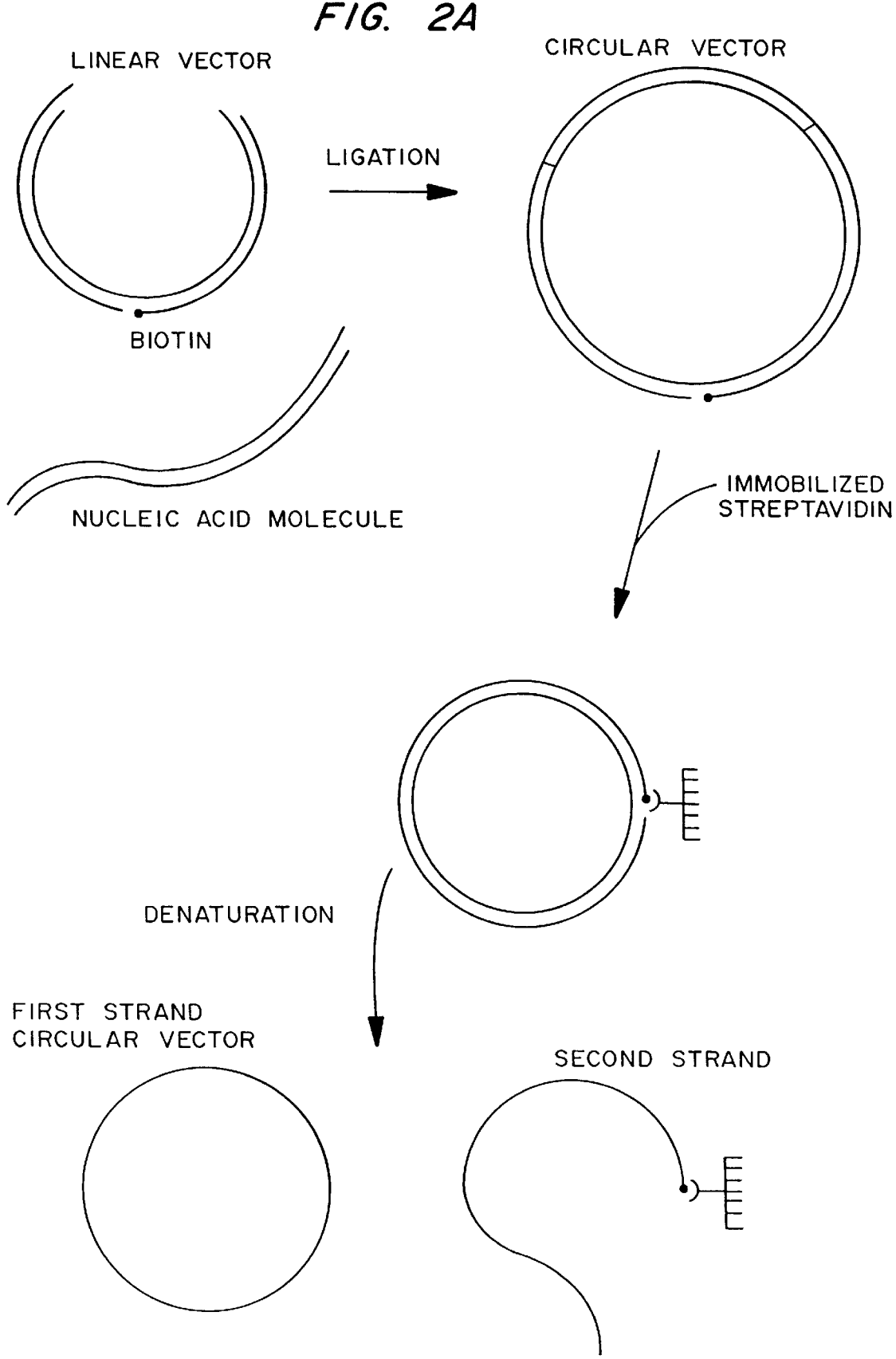
FIGS. 2A and 2B are diagrams of an example of the disclosed method where the linear vector includes an non-ligatable nick in one of its strands. Upon ligation to form a circular vector, the discontinuous strand is separated from the continuous strand by binding the biotin moiety at the nick to an immobilized streptavidin moiety.
Figure 2B:
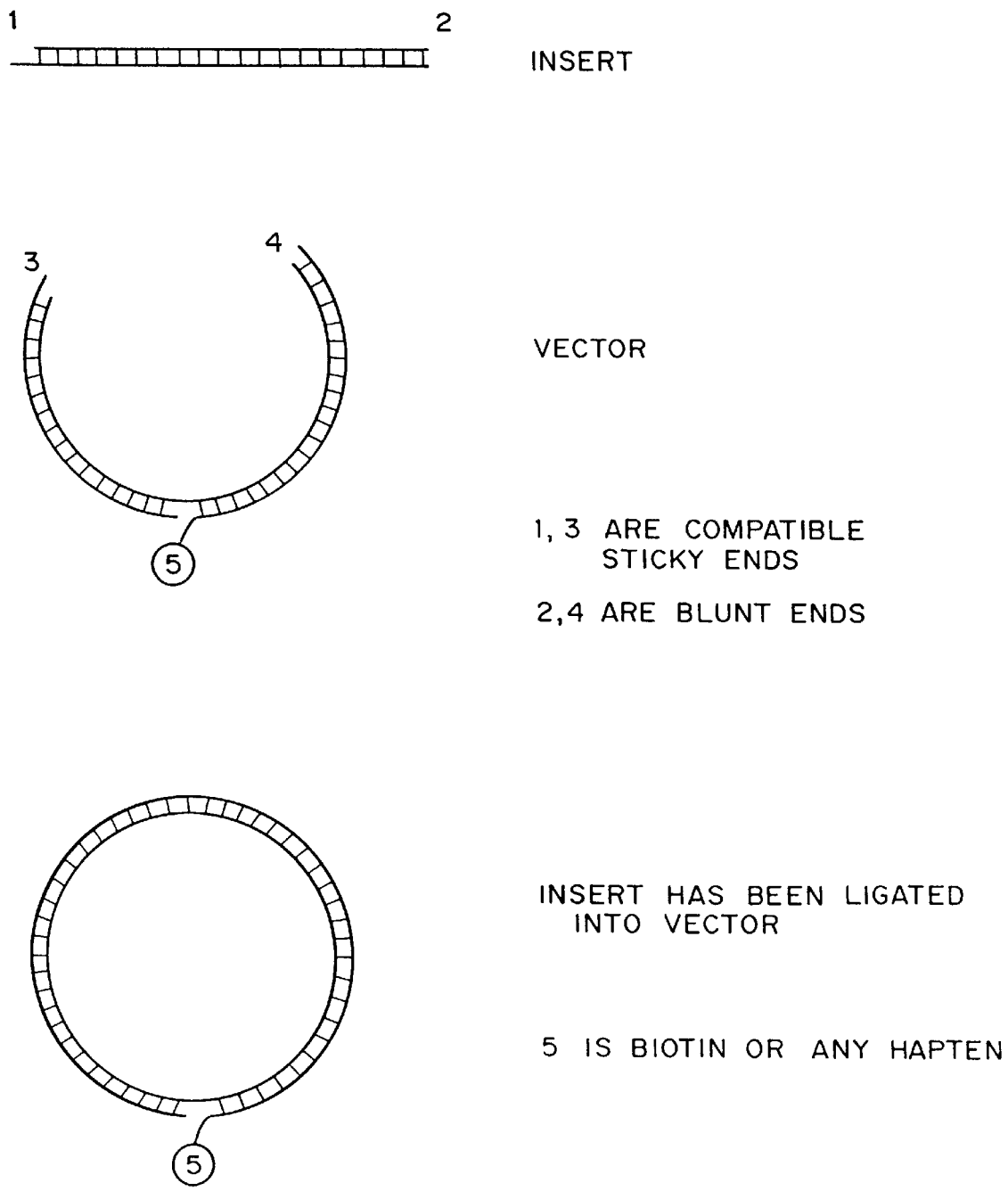

The production of a circular vector in the disclosed method is facilitated by giving the first strand and the second strand of the linear vector different characteristics. Although the linear vector is referred to as having two strands, each of these "strands" may be made up of more than one linear nucleic acid strands. That is, the first strand of the linear nucleic acid molecule may be made up of multiple nucleic acid molecules lying end to end and hybridized to the second strand. Similarly, the second strand of the linear nucleic acid molecule may be made up of multiple strands hybridized to the first strand. The use of the terms first "strand" and second "strand" are used as a convenience to refer to all of the physical nucleic acid strands that make up one side of the linear vector. The relationship of the physical strands in the linear vector to the collective first and seconds strands can be seen in FIGS. 1A–1C. The first strand of the linear vector is preferably composed of one strand. The second strand is preferably composed of more than one strand, and most preferably composed of two strands.

All of the ends present in the first strand of the linear vector, including internal ends, if present, should be ligatable. Ligatable ends are ends that can be ligated to compatible ends by ligase, or which can otherwise be coupled to compatible ends. Preferred ligatable ends are nucleotides having a 3' hydroxyl or a 5' phosphate. Internal ends are ligatable only if compatible ends are adjacent. For example, a nick with a 3' hydroxyl-on one end and a 5' phosphate on the other end is a ligatable nick and the ends are ligatable. Nick has its usual meaning. Specifically, a nick is a break in a strand hybridized to another strand where there are no unpaired nucleotides in the other strand opposite the nick.

To result in a discontinuous second strand in the circular vector, the second strand of the linear vector should contain at least one non-ligatable end or at least one gap or overlap. Non-ligatable ends are ends that cannot be ligated to compatible ends by ligase, or which cannot otherwise be coupled to compatible ends. Preferred non-ligatable ends are nucleotides having a blocking group at the 3' or 5' position. For example, the second strand of the linear vector can include a 3'-terminal or 5'-terminal biotin residue (either at the end of a continuous second strand or at a nick in a discontinuous second strand). This residue renders the terminus non-ligatable, causing all vectors to contain a nick after cloning of inserts by ligation. This biotin residue can then used as a handle to remove the second strand of the circularized vector, generating single-stranded circles for amplification. Thus, the biotin is both a blocking group and an affinity tag.

Internal ends are also non-ligatable if, for example, compatible ends are not adjacent. For example, a nick with a 3' hydroxyl on both ends is an unligatable nick and the ends are unligatable. A nick with a blocking group on one of the ends is also an unligatable nick and the end with the blocking group is an unligatable end. Both gaps and overlaps is not ligatable even if the ends would otherwise be compatible since the ends are not close enough to be coupled. Gap has its usual meaning. Specifically, a gap is a break in a strand hybridized to another strand where there is at least one nucleotide on the other strand opposite the gap that is unpaired. A gap can also occur at the end of the linear vector in that a nucleic acid molecule, when hybridized to sticky ends of the linear vector, can fail to extend to the end of one of the strands of the linear vector.

An overlap occurs where the adjacent ends of two strands hybridized adjacent to each other on another strand extend beyond the region of hybridization. A preferred form of overlap is where the two overlapping strands hybridize to each other in the overlapping region. This type of overlap in a linear vector produces a Y shaped molecule such as the one illustrated in FIGS. 1A–1C and in FIG. 3.

The second strand of the linear vector may contain multiple nicks, gaps, and overlaps in any combination. Any number of such nicks may be ligatable or non-ligatable. All that is required is at least one feature that prevents the second strand of the circular vector from being continuous following insertion of the nucleic acid molecule. For this purpose, a single non-ligatable end or other non-ligatable feature is all that is required. The first strand of the linear vector contain multiple nicks so long as they are all ligatable; that is, so long as the first strand of the circular vector will be continuous following insertion of the nucleic acid molecule.

The second strand of the linear vector can also contain one or more affinity tags to facilitate separation of the first and second strands of the circular vector formed from the linear vector. It is preferred that linear vectors include either pre-formed sticky ends or one or more restriction enzymes sites near the ends of the linear vector to facilitate insertion of nucleic acid molecules into the vectors. Multiple cloning sites (MCS) are particularly preferred. Such MCSs facilitate both insertion of a nucleic acid molecule of interest into linear vectors and removal of the nucleic acid molecule from the amplified nucleic acid. It is preferred that the ends of the linear vector, when ready for ligation, do not contain compatible ends that can be ligated. This will prevent the circularization of linear vectors in the absence of insertion of a nucleic acid molecule.

C. Circular Vectors

A circular vector is a double-stranded circular nucleic acid molecule that is a combination of a linear vector and one or more inserted nucleic acid molecules. One of the strands of the circular vector, termed the first strand, is continuous. That is, the first strand of the circular vector is a closed circular nucleic acid strand. The other strand of the circular vector, termed the second strand, is discontinuous. That is, the second strand of the circular vector is not a closed circular nucleic acid strand. The second strand can include, for example, nicks, gaps, and overlaps. The discontinuity of the second strand allows the separation of the first and second strands following denaturation. The second strand of the circular vector can also contain one or more affinity tags to facilitate separation of the first and second strands of the circular vector.

The first strand of a circular vector includes a sequence complementary to a rolling circle replication primer. This sequence is referred to as the primer complement portion of the circular vector. This facilitates amplification of the circular vector by rolling circle replication primed by the rolling circle replication primer. A separate primer complement portion is not required if the second strand of the circular vector is to serve as the rolling circle replication primer.

D. Affinity Tags

An affinity tag is a molecule that interacts specifically with a particular molecule or moiety. The molecule or moiety that interacts specifically with an affinity tag is referred to herein as an affinity target. Together, an affinity tag and affinity target make up a binding pair. Either member of a binding pair can be used as an affinity tag and either member can be used as an affinity target. An affinity tag is the member of the binding pair coupled to the linear or circular vector. A preferred binding pair is biotin and streptavidin. It is to be understood that the term affinity target refers to both separate molecules and to portions of molecules, such as an epitope of a protein, that interacts specifically with an affinity tag. Antibodies, either member of a receptor/ligand pair, and other molecules with specific binding affinities are examples of affinity tags, useful as the affinity portion of a reporter binding molecule. By coupling an affinity tag to the second strand of a linear vector, binding of the affinity tag to its affinity target allows separation of the first and second strands of the circular vector. An affinity tag that interacts specifically with a particular affinity target is said to be specific for that affinity target. For example, an affinity tag which is an antibody that binds to a particular antigen is said to be specific for that antigen. The antigen is the affinity target. Complementary nucleotide sequences can be used as binding pairs. An example of this is illustrated with the immobilization of Y shaped circular vector in FIG. 3.

E. Affinity Substrates

Affinity substrates are solid-state substrates or supports to which affinity targets have been coupled. Generally, an affinity substrate is used to facilitate separation of first and second strands of circular vectors by immobilizing the second strands of circular vectors to a solid-state substrate or support via an affinity tag. Solid-state substrates for use in affinity substrates can include any solid material to which affinity targets can be coupled. This includes materials such as acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, polyamino acids, chemical resistant metals, and corrosion resistant metals. Solid-state substrates can have any useful form including thin films or membranes, beads, bottles, dishes, fibers, woven fibers, shaped polymers, particles and microparticles. A preferred form for a solid-state substrate is a bead or surface.

Affinity targets immobilized on a solid-state substrate allow capture of the second strand of circular vectors on a affinity substrate. Such capture provides a convenient means of separating the seconds strands from the first strands of circular vectors (which are to be amplified).

Methods for immobilizing proteins, such as antibodies, to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications,* Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands,* Craig T. Hermanson et al., eds. (Academic Press, New York, 1992). Proteins, and other affinity targets having free amino groups, can be attached to a substrate by chemically cross-linking a free amino group on the protein to reactive side groups present within the solid-state substrate. For example, proteins may be chemically cross-linked to a substrate that contains free amino or carboxyl groups using glutaraldehyde or carbodiimides as cross-linker agents. In this method, aqueous solutions containing free proteins are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Methods for immobilization of oligonucleotides to solid-state substrates are well established. Oligonucleotides, including affinity targets, can be coupled to substrates using established coupling methods. For example, suitable attachment methods are described by Pease et al., *Proc. Natl. Acad. Sci. USA a* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl Acad. Sci USA* 92:6379–6383 (1995). A preferred method of attaching oligonucleotides to solid-state substrates is described by Guo et al., *Nucleic Acids Res.* 22:5456–5465 (1994).

F. Rolling Circle Replication Primer

A rolling circle replication primer (RCRP) is an oligonucleotide having sequence complementary to the primer complement portion of the first strand of a circular vector. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the circular vector. The complementary portion of a rolling circle replication primer can be any length that supports specific and stable hybridization between the primer and the primer complement portion. Generally this is 10 to 35 nucleotides long, but is preferably 16 to 20 nucleotides long. A separate rolling circle replication primer is not required if the second strand of the circular vector is to serve as the rolling circle replication primer. In this case, the second strand of the circular vector can be referred to as a rolling circle replication primer.

It is preferred that rolling circle replication primers also contain additional sequence at the 5' end of the RCRP that is not complementary to any part of the circular vector. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. The rolling circle replication primer may also include modified nucleotides to make it resistant to exonuclease digestion. For example, the primer can have three or four phosphorothioate linkages between nucleotides at the 5' end of the primer. Such nuclease resistant primers allow selective degradation of excess unligated linear vector that might otherwise interfere with hybridization of probes and primers to the amplified nucleic acid. A rolling circle replication primer can be used as the tertiary strand displacement primer in strand displacement cascade amplification.

G. Strand Displacement Primers

Primers used for strand displacement replication are referred to herein as strand displacement primers. One form of strand displacement primer, referred to herein as a secondary strand displacement primer, is an oligonucleotide having sequence matching part of the sequence of the first strand of a circular vector. This sequence is referred to as the matching portion of the strand displacement primer. This matching portion of a secondary strand displacement primer is complementary to sequences in tandem sequence DNA (TS-DNA). The matching portion of a secondary strand displacement primer may be complementary to any sequence in TS-DNA. However, it is preferred that it not be complementary TS-DNA sequence matching either the rolling circle replication primer or a tertiary strand displacement primer, if one is being used. This prevents hybridization of the primers to each other. The matching portion of a strand displacement primer may be complementary to all or a portion of the inserted nucleic acid molecule, although this is not preferred. The matching portion of a strand displacement primer can be any length that supports specific and stable hybridization between the primer and its complement. Generally this is 12 to 35 nucleotides long, but is preferably 18 to 25 nucleotides long. It is preferred that the matching portion of the circular vector is near the 3' end of the first strand of the circular vector.

It is preferred that secondary strand displacement primers also contain additional sequence at their 5' end that does not match any part of the first strand of the circular vector. This sequence is referred to as the non-matching portion of the strand displacement primer. The non-matching portion of the strand displacement primer, if present, serves to facilitate strand displacement during DNA replication. The non-matching portion of a strand displacement primer may be any length, but is generally 1 to 100 nucleotides long, and preferably 4 to 8 nucleotides long.

Another form of strand displacement primer, referred to herein as a tertiary strand displacement primer, is an oligonucleotide having sequence complementary to part of the sequence of the first strand of the circular vector. This sequence is referred to as the complementary portion of the tertiary strand displacement primer. This complementary portion of the tertiary strand displacement primer matches sequences in TS-DNA. The complementary portion of a tertiary strand displacement primer may be complementary to any sequence in the first strand of the circular vector. However, it is preferred that it not be complementary to a sequence matching the strand displacement primer. This prevents hybridization of the primers to each other. The complementary portion of a tertiary strand displacement primer can be any length that supports specific and stable hybridization between the primer and its complement. Generally this is 12 to 35 nucleotides long, but is preferably 18 to 25 nucleotides long. It is preferred that tertiary strand displacement primers also contain additional sequence at their 5' end that is not complementary to any part of the first strand of the circular vector. This sequence is referred to as the non-complementary portion of the tertiary strand displacement primer. The non-complementary portion of the tertiary strand displacement primer, if present, serves to facilitate strand displacement during DNA replication. The non-complementary portion of a tertiary strand displacement primer may be any length, but is generally 1 to 100 nucleotides long, and preferably 4 to 8 nucleotides long. A rolling circle replication primer is a preferred form of tertiary strand displacement primer. It is preferred that the complementary portion of the circular vector is near the 5' end of the first strand of the circular vector.

Strand displacement primers may also include modified nucleotides to make them resistant to exonuclease digestion. For example, the primer can have three or four phosphorothioate linkages between nucleotides at the 5' end of the primer. Such nuclease resistant primers allow selective degradation of excess unligated linear vectors that might otherwise interfere with hybridization of probes and primers to the amplified nucleic acid. Strand displacement primers can be used for strand displacement replication and strand displacement cascade amplification, both described below.

H. Synthesis of Oligonucleotides

Linear vectors, rolling circle replication primers, strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, MA or ABI Model 380B). Synthetic methods useful for making oligonucleotides are also described by Ikuta et al., *Ann Rev. Biochem.* 53:323–356 (1984), (phosphotriester and phosphite-triester methods), and Narang et al., *Methods Enzymol.* 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

I. DNA ligases

Any DNA ligase is suitable for use in the disclosed method. Preferred ligases are those that preferentially form phosphodiester bonds at nicks in double-stranded DNA. That is, ligases that fail to ligate the free ends of single-stranded DNA at a significant rate are preferred. Thennostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J Biol. Chem.* 253:4590–4592 (1978)), AMPLIGASE® (Kalin et al., *Mutat Res.*, 283(2):119–123 (1992); Winn-Deen et al., *Mol Cell Probes* (England) 7(3):179–186 (1993)), Taq DNA ligase (Barany, *Proc. Natl. Acad Sci. USA* 88:189–193 (1991), *Thermus thermophilus* DNA ligase (Abbott Laboratories), *Thermus scotoductus* DNA ligase and *Rhodothermus marinus* DNA ligase (Thorbjarnardottir et al., *Gene* 151:177–180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction,* American Association for the Study of Liver Diseases (Chicago, IL, Nov. 3–7, 1995)).

J. DNA polymerases

DNA polymerases useful in rolling circle replication must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the circular vector. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), VENT® DNA polymerase (Kong et al., *J Biol. Chem.* 268:1965–1975 (1993)), Klenow fragment of DNA polymerase I (Jacobsen et al., *Eur. J. Biochem.* 45:623–627 (1974)), T5 DNA polymerase (Chatteijee et al., *Gene* 97:13–19 (1991)), PRD1 DNA polymerase (Zhu and Ito, *Biochim. Biophys. Acta.* 1219:267–276 (1994)), modified T7 DNA polymerase (Tabor and Richardson, *J Biol Chem.* 262:15330–15333 (1987); Tabor and Richardson, *J Biol Chem.* 264:6447–6458 (1989); Sequenase™ (U.S. Biochemicals)), and T4 DNA polymerase holoenzyme (Kaboord and Benkovic, *Curr. Biol.* 5:149–157 (1995)). φ29 DNA polymerase is most preferred. Rolling circle DNA polymerases are also generally useful for strand displacement replication.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al., *J. Virology* 67(12):7648–7653 (1993)), adenovirus DNA-binding protein (Zijderveld and van der Vliet, *J. Virology* 68(2): 1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)), single-stranded DNA binding proteins (SSB; Rigler and Romano, *J. Biol. Chem.* 270:8910–8919 (1995)), and calf thymus helicase (Siegel et al., *J. Biol Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995).

It is possible to enhance the specificity of the DNA amplification reactions used in the disclosed method by using a DNA polymerase that is inactive at low temperature, and active only at high temperature. An example of such an enzyme, AmpliTaq Gold, has been described by Moretti et al., *Biotechniques* 25:716–722 (1998). AmpliTaq Gold is inactive until heated during the PCR before thermal cycling. A similar enzyme could be used in the disclosed method. Temperature activation of DNA polymerase can also be achieved using antibodies specific for the polymerase. For example, antibodies specific for Bst large fragment DNA polymerase could be obtained by immunization of mice. Among such antibodies, one could be chosen on the basis of its ability to bind to and inhibit the enzyme at room temperature. The antibody could also be chosen, using known screening procedures, such that upon heating, the inhibition of the DNA polymerase would cease. Combining the antibody with Bst large fragment DNA polymerase would generate an enzyme mixture that is activated upon heating.

K. Kits

Any combination of the materials useful in the disclosed method can be packaged together as a kit for performing the disclosed method. In particular, linear vectors, rolling circle replication primers, affinity substrates, and strand displacement primers are useful components of such kits. Enzymes necessary for the disclosed method are also preferred components of such kits.

L. Tandem Sequence DNA

The first strand of the circular vector, when replicated, gives rise to a long DNA molecule containing multiple repeats of sequences complementary to the circular vector. This long DNA molecule is referred to herein as tandem sequences DNA (TS-DNA). TS-DNA contains sequences complementary to the inserted nucleic acid molecule and the primer complement portion. If the tandem sequence DNA is itself replicated by strand displacement amplification, the resulting long DNA molecules containing multiple repeats of sequences matching the circular vector are referred to as secondary tandem sequence DNA. If the secondary tandem sequence DNA is in turn replicated by strand displacement amplification, the resulting long DNA molecules containing multiple repeats of sequences complementary to the circular vector are referred to as tertiary tandem sequence DNA.

M. Collected Samples (Library Replica)

The usefulness of the disclosed method is increased by producing libraries of clones and saving samples of the clones for later use. Such samples are referred to a collected samples. Collecting samples is analogous to replica plating in cell-based cloning. Samples of amplified nucleic acid can be collected, for example, by transfer with an array of pins (most useful when the nucleic acid is amplified in an array pattern), by transfer into an array, by direct transfer from a spread of amplified nucleic acid on a surface to another surface (this is analogous to colony transfer), and by blotting the amplified nucleic acid unto a membrane (most useful when the nucleic acid is amplified in agarose). Once the samples are collected, they can be further amplified to allow analysis or use of the clones, or to allow another round of replica collection.

II. Method

The disclosed method involves inserting nucleic acid molecules of interest into a linear vector to form a circular vector with one continuous strand and one discontinuous strand. The discontinuous strand may include an affinity tag which, by interaction with an affinity substrate, can facilitate separation of the continuous strand from the discontinuous strand. The continuous strand of the circular vector is amplified by rolling circle replication to form tandem sequence DNA. Rolling circle replication is primed by a rolling circle replication primer complementary to a sequence in the continuous strand. The tandem sequence DNA itself may be amplified by strand displacement replication, to form secondary tandem sequence DNA, using strand displacement primers (complementary to a sequence in the tandem sequence DNA). The secondary tandem sequence DNA may also be amplified by strand displacement replication, to form tertiary tandem sequence DNA, using strand displacement primers or the rolling circle replication primers (complementary to a sequence in the secondary tandem sequence DNA). The amplified DNA can be sequenced, probed, subjected to restriction analysis, subcloned, transcribed, subjected to hybridization or denaturation analysis, further amplified, or stored.

Multiple amplification reactions can be carried out in parallel, preferably in arrays or as spreads of diluted vectors on surfaces or embedded in agarose. The resulting "colonies" of amplified DNA represent molecular clones of the progenitor circular vectors with an inserted nucleic acid molecule. Collectively, such colonies form a library of cloned nucleic acid molecules that can be replica plated or arrayed, stored, and screened. These procedures are described in detail below.

When using the disclosed method to produce a library of cDNA molecules, or to analyze mRNA in a sample via cDNA, the cDNA preparations used for cloning in the disclosed vectors can be prepared using methods that reduce the over-representation of cDNA that corresponds to highly abundant messenger RNA. Libraries made using such methods are called normalized libraries (Bonaldo et al., *Genome Res* 6:791–806 (1996)). The use of normalized libraries reduces the number of clones that must be screened to find a sequence of interest.

A. Ligation

Ligation of nucleic acid molecules into linear vectors can be accomplished using any suitable conditions. Techniques for insertion of nucleic acid molecules into vectors in general are well established and can be used with the disclosed linear vectors. Suitable ligases for the ligation operation are described above. Ligation reactions can involve a single type of linear vector and a single type of nucleic acid molecule to be inserted, a single type of linear vector and multiple different types of nucleic acid molecules to be inserted, multiple types of linear vector and a single type of nucleic acid molecule to be inserted, or multiple types of linear vectors and multiple types of nucleic acid molecules to be inserted. For general cloning and production of nucleic acid libraries it is preferred that a single type of linear vector and multiple different types of nucleic acid molecules to be inserted be used. For subcloning of specific nucleic acid fragments it is preferred that a single type of linear vector and a single type of nucleic acid molecule to be inserted. Ligation conditions are generally known. Most ligases require $Mg^{++}$. There are two main types of ligases, those that are ATP-dependent and those that are NAD-dependent. ATP or NAD, depending on the type of ligase, should be present during ligation.

Ligation of compatible ends of nucleic acid molecules and vectors can be facilitated through the use of blunt ends or sticky ends as is known in the field of molecular cloning. Both blunt ends and sticky ends can be produced by digestion of the nucleic acid molecules and the linear vectors with appropriate restriction enzymes, by ligation of appropriate linkers to the ends of the nucleic acid molecules and the linear vectors, or both. In the case of linear vectors, appropriate ends can be formed directly by the structure of the linear vector without the need for restriction enzyme digestion of linker ligation. In the case of the nucleic acid molecules to be inserted, appropriate ends can be appended to the ends during preparation of the nucleic acid molecule. For example, appropriate ends can be incorporated into cDNA by using primer having appropriate sequences during cDNA synthesis or by adding a nucleotide tail to the cDNA.

B. Amplification

The circular vectors formed by ligation of linear vectors and nucleic acid molecules of interest serve as substrates for a rolling circle replication. This reaction requires the addition of two reagents: (a) a rolling circle replication primer, which is complementary to the primer complement portion of the first strand of the circular vector, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 25 tandem copies of a sequence complementary to a 4000 bp circular vector. This tandem sequence DNA (TS-DNA) consists of alternating vector sequence and insert sequence. As an alternative, the second strand of the circular vector can serve as the rolling circle replication primer.

During rolling circle replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al., *Proc. Natl. Acad. Sci. USA* 78:6633 (1981)).

Strand displacement replication is a way to amplify TS-DNA. Strand displacement replication is accomplished by hybridizing strand displacement primers to TS-DNA and allowing a DNA polymerase to synthesize DNA from these primed sites. The product of strand displacement replication is referred to as secondary tandem sequence DNA or TS-DNA-2. Strand displacement replication can be accomplished by performing rolling circle replication to produce TS-DNA, and then mixing strand displacement primer with the TS-DNA and incubating to replicate the tandem sequence DNA. The strand displacement primer is complementary to a part of the circular vector used to generated TS-DNA as described earlier. It is preferred that the strand displacement primer is not complementary to the rolling circle replication primer, or to a tertiary strand displacement primer, if used.

Strand displacement replication can also be carried out simultaneously with rolling circle replication. This is accomplished by mixing strand displacement primer with the circular vector and rolling circle replication primer prior to incubating the mixture for rolling circle replication. For simultaneous rolling circle replication and strand displacement replication, it is preferred that the rolling circle DNA polymerase be used for both replications. This allows optimum conditions to be used and results in displacement of other strands being synthesized downstream. Generally, strand displacement replication can be performed by, simultaneous with or following rolling circle replication, mixing a strand displacement primer with the TS-DNA and incubating to replicate the tandem sequence DNA to result in the formation of secondary tandem sequence DNA.

To optimize the efficiency of strand displacement replication, it is preferred that a sufficient concentration of strand displacement primer be used to obtain sufficiently rapid priming of the growing TS-DNA strand to out-compete any remaining unligated linear vectors that might be present for binding to TS-DNA. In general, this is accomplished when the strand displacement primer is in very large excess compared to the concentration of single-stranded sites for hybridization of the strand displacement primer on TS-DNA. Optimization of the concentration of strand displacement primer can be aided by analysis of hybridization kinetics using methods such as those described by Young and Anderson, "Quantitative analysis of solution hybridization" in *Nucleic Acid Hybridization: A Practical Approach* (IRL Press, 1985) pages 47–71. Alternatively, the efficiency of strand displacement replication can be improved by the removal of unligated linear vectors prior to amplification of the TS-DNA. In strand displacement replication, it is preferred that the concentration of strand displacement primer generally be from 500 nM to 5000 nM, and most preferably from 700 nM to 1000 nM.

As a strand displacement primer is elongated, the DNA polymerase will run into the 5' end of the next hybridized strand displacement molecule and will displace its 5' end. In this fashion a tandem queue of elongating DNA polymerases is formed on the TS-DNA template. As long as the rolling circle reaction continues, new strand displacement primers and new DNA polymerases are added to TS-DNA at the growing end of the rolling circle.

When strand displacement replication is carried out in the presence of a tertiary strand displacement primer, an exponential amplification of TS-DNA sequences takes place. This special and preferred mode of strand displacement replication is referred to as strand displacement cascade amplification (SDCA). In SDCA, a strand displacement primer primes replication of TS-DNA to form TS-DNA-2, as described above. The tertiary strand displacement primer can then hybridize to, and prime replication of, TS-DNA-2 to form TS-DNA-3 (tertiary tandem sequence DNA). Strand displacement of TS-DNA-3 by the adjacent, growing TS-DNA-3 strands makes TS-DNA-3 available for hybridization with secondary strand displacement primer. This results in another round of replication resulting in TS-DNA-4 (which is equivalent to TS-DNA-2). TS-DNA-4, in turn, becomes a template for DNA replication primed by tertiary strand displacement primer. The cascade continues this manner until the reaction stops or reagents become limiting. This reaction amplifies DNA at an almost exponential rate, although kinetics are not truly exponential because there are stochastically distributed priming failures, as well as steric hindrance events related to the large size of the DNA network produced during the reaction.

In a preferred mode of SDCA, the rolling circle replication primer serves as the tertiary strand displacement primer, thus eliminating the need for a separate primer. For this mode, the rolling circle replication primer should be used at a concentration sufficiently high to obtain rapid priming on the growing TS-DNA-2 strands. To optimize the efficiency of SDCA, it is preferred that a sufficient concentration of secondary strand displacement primer and tertiary strand displacement primer be used to obtain sufficiently rapid priming of the growing TS-DNA strand to out-compete TS-DNA for binding to its complementary TS-DNA, and, in the case of secondary strand displacement primer, to out-compete any remaining unligated linear vector that might be present for binding to TS-DNA. In general, this is accomplished when the secondary strand displacement primer and tertiary strand displacement primer are both in very large excess compared to the concentration of single-stranded sites for hybridization of the strand displacement primers on TS-DNA. For example, it is preferred that the secondary strand displacement primer is in excess compared to the concentration of single-stranded secondary strand displacement primer complement sites on TS-DNA, TS-DNA-3, TS-DNA-5, and so on. In the case of tertiary strand displacement primer, it is preferred that the tertiary strand displacement primer is in excess compared to the concentration of single-stranded tertiary strand displacement primer complement sites on TS-DNA-2, TS-DNA-4, TS-DNA-6, and so on. Such an excess generally results in a primer hybridizing to its complement in TS-DNA before amplified complementary TS-DNA can hybridize. Optimization of primer concentrations can be aided by analysis of hybridization kinetics (Young and Anderson). In a strand displacement cascade amplification, it is preferred that the concentration of both secondary and tertiary strand displacement primers generally be from 500 nM to 5000 nM, and most preferably from 700 nM to 1000 nM.

As in the case of secondary strand displacement primers, if the concentration of DNA polymerase is sufficiently high, the polymerase will initiate DNA synthesis at each available 3' terminus on the hybridized tertiary strand displacement primers, and these elongating TS-DNA-3 molecules will block any hybridization by TS-DNA-2. As a tertiary strand displacement primer is elongated to form TS-DNA-3, the DNA polymerase will run into the 5' end of the next hybridized tertiary strand displacement primer molecule and will displace its 5' end. In this fashion a tandem queue of elongating DNA polymerases is formed on the TS-DNA-2 template. As long as the reaction continues, new rolling circle replication primers and new DNA polymerases are added to TS-DNA-2 at the growing ends of TS-DNA-2. This hybridization/replication/strand displacement cycle is repeated with hybridization of secondary strand displacement primers on the growing TS-DNA-3.

Generally, strand displacement cascade amplification can be performed by, simultaneous with, or following, rolling circle replication, mixing a secondary strand displacement primer and a tertiary strand displacement primer with the TS-DNA and incubating to replicate the tandem sequence DNA—where replication of the tandem sequence DNA results in the formation of secondary tandem sequence DNA and where replication of the secondary tandem sequence DNA results in formation of tertiary tandem sequence DNA (TS-DNA-3).

Strand displacement replication can also be carried out sequentially. Following a first round of strand displacement replication, a tertiary strand displacement primer can be mixed with the TS-DNA and TS-DNA-2 and incubated to replicate the secondary tandem sequence DNA, where replication of the secondary tandem sequence DNA results in formation of tertiary tandem sequence DNA (TS-DNA-3). This round of strand displacement replication can be referred to as tertiary strand displacement replication. However, all rounds of strand displacement replication following rolling circle replication can also be referred to collectively as strand displacement replication.

A modified form of strand displacement replication results in amplification of TS-DNA and is referred to as opposite strand amplification (OSA). OSA is the same as strand displacement replication except that a special form of rolling circle replication primer is used that prevents it from hybridizing to TS-DNA-2. This can be accomplished in a number of ways. For example, the rolling circle replication primer can have an affinity tag coupled to its non-complementary portion allowing the rolling circle replication primer to be removed prior to strand displacement replication. Alternatively, remaining rolling circle replication primer can be crippled following initiation of rolling circle replication. One preferred form of rolling circle replication primer for use in OSA is designed to form a hairpin that contains a stem of perfectly base-paired nucleotides. The stem can contain 5 to 12 base pairs, most preferably 6 to 9 base pairs. Such a hairpin-forming rolling circle replication primer is a poor primer at lower temperature (less than 40° C.) because the hairpin structure prevents it from hybridizing to complementary sequences. The stem should involve a sufficient number of nucleotides in the complementary portion of the rolling circle replication primer to interfere with hybridization of the primer to the circular vector. Generally, it is preferred that a stem involve 5 to 24 nucleotides, and most preferably 6 to 18 nucleotides, of the complementary portion of a rolling circle replication primer. A rolling circle replication primer where half of the stem involves nucleotides in the complementary portion of the rolling circle replication primer and the other half of the stem involves nucleotides in the non-complementary portion of the rolling circle replication primer is most preferred. Such an arrangement eliminates the need for self-complementary regions in the circular vector when using a hairpin-forming rolling circle replication primer.

If an excess of tertiary tandem sequence DNA is desired, the secondary strand displacement primer can be crippled in the same manner as is described above for the rolling circle replication primer (the rolling circle replication primer and tertiary strand displacement primer should not be crippled in this case). The reaction at the higher, permissive temperature should be carried out long enough to produce a reasonable amount of secondary tandem sequence DNA to serve as a template for tertiary sequence DNA. When the temperature is shifted, the secondary strand displacement primer can no longer prime synthesis and the synthesis of tertiary tandem sequence DNA soon outstrips the amount of secondary tandem sequence DNA. Of course tandem sequence DNA will continue to be produced by rolling circle replication throughout the reaction (since the rolling circle replication primer is not crippled).

When starting the rolling circle replication reaction, secondary strand displacement primer and rolling circle replication primer are added to the reaction mixture, and the solution is incubated briefly at a temperature sufficient to disrupt the hairpin structure of the rolling circle replication primer but to still allow hybridization to the primer complement portion of the circular vector (typically greater than 50° C.). This incubation permits the rolling circle replication primer to hybridize to the primer complement portion of the circular vector. The solution is then brought to the proper temperature for rolling circle replication, and the rolling circle DNA polymerase is added. As the rolling circle reaction proceeds, TS-DNA is generated, and as the TS-DNA grows in length, the secondary strand displacement primer rapidly initiates DNA synthesis with multiple strand displacement reactions on TS-DNA. These reactions generate TS-DNA-2, which is complementary to the TS-DNA. While TS-DNA-2 contains sequences complementary to the rolling circle replication primer, the primer is not able to hybridize nor prime efficiently at the reaction temperature due to its hairpin structure at this temperature. Thus, there is no further priming by the rolling circle replication primer and the only products generated are TS-DNA and TS-DNA-2. The reaction comes to a halt as rolling circle amplification stops and TS-DNA becomes completely double-stranded. In the course of the reaction, an excess of single-stranded TS-DNA-2 is generated.

Another form of rolling circle replication primer useful in OSA is a chimera of DNA and RNA. In this embodiment, the rolling circle primer has deoxyribonucleotides at its 3' end and ribonucleotides in the remainder of the primer. It is preferred that the rolling circle replication primer have five or six deoxyribonucleotides at its 3' end. By making part of the rolling circle replication primer with ribonucleotide, the primer can be selectively degraded by RNAse H when it is hybridized to DNA. Such hybrids form during OSA as TS-DNA-2 is synthesized. The deoxyribonucleotides at the 3' end allow the rolling circle DNA polymerase to initiate rolling circle replication. RNAse H can then be added to the OSA reaction to prevent priming of TS-DNA-2 replication.

Unligated linear vectors may be removed prior to rolling circle replication to eliminate competition between unligated linear vectors and the secondary strand displacement primer for hybridization to TS-DNA. Alternatively, the concentration of the secondary strand displacement primer can be made sufficiently high so that it out-competes unligated linear vector for hybridization to TS-DNA. This allows strand displacement replication to be performed without removal of unligated linear vectors.

C. Separation

Once the linear vector and nucleic acid molecule are circularized to form a circular vector with one continuous strand and one discontinuous strand, it is preferred that the continuous strand of the circular vector (a single-stranded, closed circular nucleic acid molecule susceptible to rolling circle replication) is separated from the discontinuous strand of the circular vector. Separation allows rolling circle replication to proceed more efficiently.

It is preferred that the two strands of the circular vector are separated by immobilizing the discontinuous (second) strand of the circular vector and then denaturing and washing away the continuous (first) strand of the circular vector. This can be accomplished, for example, by including an affinity tag in the second strand of the circular vector which can then be bound to an immobilized affinity target, thus immobilizing the second strand of the circular vector. For this purpose, use of biotin as an affinity tag and streptavidin as an affinity target is preferred.

Figure 3:
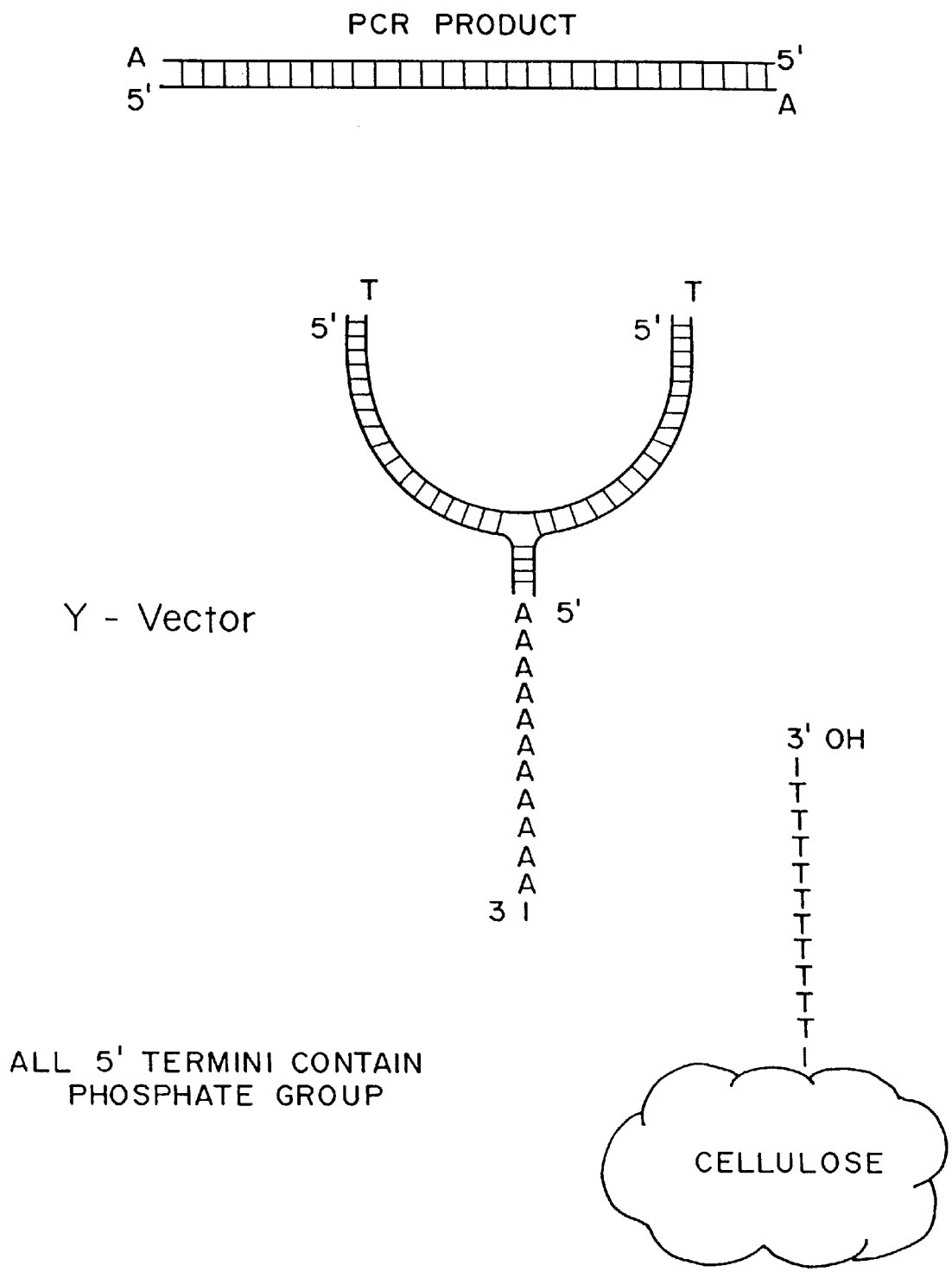
FIG. 3 is a diagram of an example of the disclosed method where the linear vector has an overlap. Upon ligation to form a circular vector (with a Y tail), the discontinuous strand is separated from the continuous strand by ligating one end of the discontinuous strand to an immobilized nucleic acid probe. This ligation is mediated by hybridization between the single-stranded extension of the discontinuous strand and the probe.
Figure 4:
FIG. 4 is a diagram of an example of the disclosed method where the linear vector is a linker having sticky ends compatible with sticky ends formed by restriction digestion of PCR primer sequences incorporated at the ends of PCR amplified DNA. The linker facilitates circularization of the PCR amplified DNA. The linker has one non-ligatable end which, upon ligation, results in a circular molecule with one continuous strand and one discontinuous strand. The discontinuous strand is separated from the continuous strand by binding the biotin moiety at the nick to an immobilized streptavidin moiety.
Figure 4:
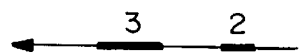
Figure 4:
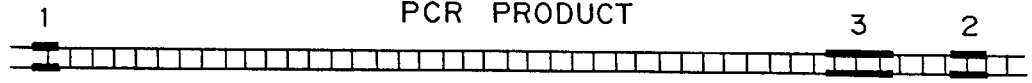
Figure 4:
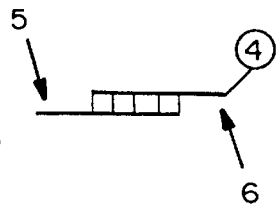
Figure 4:
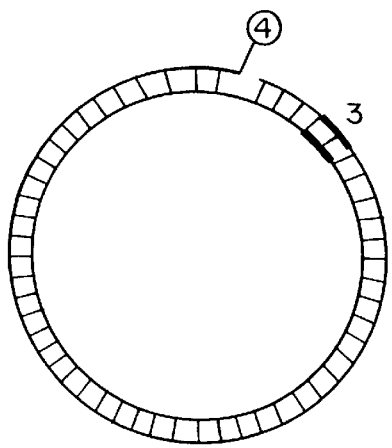

Complementary oligonucleotides can also be used as binding pairs for separating the first and second strands of the circular vector. An oligonucleotide affinity tag that is a part of or coupled to the second strand of the circular vector is hybridized to an immobilized complementary oligonucleotide. The oligonucleotide affinity tag is preferably an unhybridized tail in an overlap in the second strand of the circular vector (see FIG. 3). It is preferred that the oligonucleotide affinity tag be ligated or otherwise coupled to a solid-state substrate or support to keep the second strand immobilized during denaturation. This can be accomplished, for example, by using a circular vector with a staggered tail in the second strand and an immobilized oligonucleotide that can hybridize to the longer strand of the tail such that the end of the immobilized oligonucleotide can be ligated to the shorter strand of the staggered tail. An example of such an arrangement is shown in FIG. 3.

The first and second strands of the circular vector can be denatured using any suitable means. Preferred conditions for denaturation include the use of heat, alkaline conditions, chaotropic conditions, and combinations. These and other means of nucleic acid denaturation are known and can be used in the disclosed method. Washing and collection of the first strand is performed during or after denaturation.

As an example, the first and second strands of circular can be separated using a two-step procedure. First, the circular vector, which contains a biotin residue on the second strand, is bound to beads containing streptavidin, in order to bind the vector via the biotin. The beads are then washed with fornamide at mildly alkaline pH. Under appropriate conditions, the circular vector, which contains an unligated nick site by design, separates into two DNA molecules. Thus, alkaline denaturation releases free single-stranded circles from the beads. The single-stranded circular molecules (that is, the first strands of the circular vector) are then further purified by gel filtration or ion exchange (Mono-Q 5/5) chromatography in the presence of an alkaline buffer (15 mM NaOH). This purification step will remove small circles, and small linear vector molecules that contaminate the circular vectors with inserts.

D. Removing Linear Nucleic Acids

Unligated linear nucleic acids, including unligated linear vector, can be removed prior to rolling circle replication. In addition to methods described elsewhere herein, the gene 6 exonuclease of phage T7 provides a useful tool for the elimination of linear nucleic acids that might bind to the TS-DNA. This exonuclease digests DNA starting from the 5' end of a double-stranded structure. It has been used successfully for the generation of single-stranded DNA after PCR amplification (Holloway et al., *Nucleic Acids Res.* 21:3905–3906 (1993); Nikiforov et al., *PCR Methods and applications* 3:285–291(1994)). This enzyme can be added after ligation, together with the rolling circle DNA polymerase. To protect TS-DNA from degradation, the rolling circle replication primer can contain 3 or 4 phosphorothioate linkages at the 5' end, to make this molecule resistant to the exonuclease (Nikiforov et al. (1994)). The exonuclease will degrade unprotected linear molecules as they become associated with the rolling circle DNA product.

E. Dilution and Division

The disclosed method is particularly useful for creation of a library of cloned nucleic acid molecules. For this purpose it is useful to dilute and divide ligated vectors containing inserts to separate individual circular vectors and allow production of clonal "colonies" of nucleic acid amplified from a single circular vector. It is preferred that a solution containing circular vectors is diluted sufficiently such that amplification reactions contain, on average, a single circular vector. This can be accomplished, for example, by making a range of dilutions, dividing the diluted vector solutions among reactions, and performing amplification. The dilution is considered optimal when about 33% of the reactions produce amplified nucleic acid. This follows from well known distribution statistics.

The division of the diluted circular vectors can be accomplished in several ways. For example, the diluted solution can be spotted as an array on a surface. The diluted solution can also be spread on a surface with the circular vectors becoming separated. The diluted solution can also be mixed with agarose and spread on a surface. A preferred way to divide the diluted circular vectors is to use a microarray of very small liquid droplets on a glass surface. The microdroplet arrays contain the diluted circular vectors, and enable the generation of DNA clones in very small compartments, without the need for physical barriers such as tubes or wells.

One useful way to combine division of the ligation reaction with amplification is to spread the ligation reaction (diluted or not as appropriate) on a surface and then to spot amplification reaction components (that is, buffers, reagents, polymerase) on the surface in an array. Techniques for spotting are described, for example, in U.S. Pat. No. 5,807,522 to Brown et al. The method here differs, however, in that it is the reaction components, rather than individual samples, that are spotted. All of the spotted material is identical. The amplification reagents will then cause amplification of whatever nucleic acid is present at the location of each spot of reagents. The nucleic acid on the surface comes from the spread of the ligation reaction.

As an example of spreading, the ligated DNA can be diluted serially to obtain concentrations in the range of several million molecules per milliliter. Approximately 22 μl of this DNA solution (containing approximately 30,000 to 120,000 DNA molecules) is placed on a cover slip, and covered with a polylysine-coated microscope slide. The DNA is allowed to bind the polylysine-covered surface for 30 minutes at 37° C. The slide then dipped in 0.01% Tween-20, and dried at room temperature. Using an arraying instrument, an array is constructed consisting of 6000 individual micro-droplets of a solution containing the four dideoxynucleoside triphosphates, a suitable buffer, and enzymes for amplification. The diameter of the droplets can be approximately 0.150 millimeters. Droplets preferably are dispensed on the surface of the slide in a controlled humidity atmosphere, in order to maintain a constant droplet volume during amplification. Alternatively, the diluted circular vectors may be placed on the glass surface using the arrayer instrument to dispense small volumes that on the average contain a single ligated DNA molecule. It can be calculated that when 33% of the droplets grow molecular colonies, and the rest do not grow anything, most colonies are likely to be of clonal origin. Adjusting the initial inoculum density, it should be possible to obtain up to 1500 clonal colonies per 6000-droplet array.

As an example of agarose spreading, dilutions of the vectors can be mixed with a buffer containing melted agarose at 60° C. and overlaying the solution on a petri dish to form a thin agarose layer (0.2 to 2% agarose), such that the concentration of the vectors is in the range of 500 to 5,000 per plate. The embedded vectors can then be amplified using the disclosed method. At appropriate dilutions, DNA molecular colonies clonally derived from single vectors will form in the thin film of agarose. The initial density of seed DNA molecules should be such that the DNA molecular colonies do not overlap. One useful technique of agarose spreading is describe in U.S. Pat. No. 5,616,478 to Chetverin et al.

F. Sample Collection (Replica Plating)

The usefulness of the disclosed method is increased by producing libraries of clones and saving samples of the clones for later use. Such samples are referred to as collected samples. Collecting samples is analogous to replica plating in cell-based cloning. Samples of amplified nucleic acid can be collected, for example, by transfer with an array of pins (most useful when the nucleic acid is amplified in an array pattern), by transfer into an array, by direct transfer from a spread of amplified nucleic acid on a surface to another surface (this is analogous to colony transfer), and by blotting the amplified nucleic acid unto a membrane (most useful when the nucleic acid is amplified in agarose). Once the samples are collected, they can be fuirther amplified to allow analysis or use of the clones, or to allow another round of replica collection.

Where droplet arrays are used, the molecular colonies (that is, the droplets following amplification) can be replicated by contacting the array with a multi-pin replicator that will bind only a fraction of the volume of the micro-droplet. Colony replicas may be stored by blotting the replicator on a membrane such as nitrocellulose of NA-45 (S&S). A preferred way to store replicas is to contact the replicator with a polylysine-coated glass slide, which will permit hybridization or primer extension sequencing with fluorescent probes. Replicas of reaction droplets on a surface can also be made by contacting a second surface with the droplets. In general, it is preferred that the second surface contact only the droplets and not the first surface. Replicas of spreads of nucleic acids on a surface likewise can be made by contacting a second surface with the spread.

Replicas of amplified nucleic acid bound covalently to glass can be made using any suitable coupling procedure. For example, in order to facilitate a subsequent step of covalent binding to a glass surface, each of the two strand displacement replication primers used for the strand displacement cascade amplification of circular vectors may be synthesized with a primary amino group at the 5' end. At the end of the amplification reaction, the glass slide will contain thousands of liquid droplets harboring DNA clones, and all the DNA molecules will contain 5'-terminal reactive amino groups. At this point the glass slide can be contacted with another glass slide, leaving an air gap of less than 1 mm (defined by the thickness of a plastic spacer), in such a manmer that the glass slide on top will contact all of the liquid droplets without excessive compression. The lower face of this slide (the upper slide) can be derivatized using the methods described by Guo et al., *Nucleic Acids Research* 22:5456–5465 (1994), Guo et al., *Nature Biotechnology* 15:331–335 (1997)), Guo et al., *Nucleic Acids Res* 22:5456–5465 (1994), or Beier and Hoheisel, *Nucleic Acids Res* 27:1970–1977 (1999), to make the glass surface chemically reactive. The two-slide sandwich is incubated for 1 to 2 hours at 37° C. (or as appropriate for the derivative chemistry involved) in order to obtain covalent coupling of the amplified DNA contained in each droplet to the lower face of the upper slide.

Where agarose has been used to form molecular colonies, analysis of the colonies can be facilitated by blotting the amplified nucleic acid unto a membrane or other blotting surface. Many such blotting techniques are known and can be used with the disclosed method. For example, the agarose film can be placed in a vacuum-blotting device that contacts both the bottom and the top of the agarose film. The nucleic acid on the agarose film can then be vacuum-blotted to two membranes simultaneously, one placed on top of the agarose and the other below the agarose, to generate two replicas of the molecular colonies on the surface of the membrane.

G. Detecting Amplified Nucleic Acid Molecules

The amplified nucleic acid can be used for any purpose for which nucleic acids can be used. For example, the nucleic acid can be sequenced, probed, subjected to restriction analysis, subcloned, transcribed, subjected to hybridization or denaturation analysis, further amplified, or stored. Diagnostic methods, such as sequencing and probing for specific sequences, are preferred. For these purposes, the amplified nucleic acid can be analyzed using standard molecular biology procedures, such restriction enzyme digestion, cloning in a plasmid vector, PCR amplification, which are well known.

Libraries of cloned nucleic acids formed by the disclosed method can be screened using any of the methods used for screening conventional libraries. For example, cDNA libraries made using the disclosed method can be analyzed using conventional screens. Libraries can also be used for in situ transcription to generate RNA colonies, which can then be analyzed (in situ or in replicas) by appropriate screens, such as aptamer screens or ribozyme activity screens. Libraries can also be screened by in situ translation on array replicas (see, for example, Saris et al., *Nucleic Acids Res.* 10:4831–4843 (1982)). Libraries can also be screened by in situ coupled transcription-translation systems, and subsequent catalytic activity assays for the analysis of mutagenized enzymes.

The disclosed method can also be used for serial analysis of gene expression (SAGE), making it more efficient by streamlining the cloning and sequencing into a single process stream. This method involves amplification of cDNA inserted into linear vectors as described herein prior to the SAGE analysis. This means of amplification is useful since PCR amplification of the cDNA prior to cloning, which can skew the abundance of cDNA sequences due to differential amplification, is avoided. The disclosed method insures that sequence tag frequencies in the clone population (which are measured in SAGE) reflect the original frequencies of the cDNAs.

The method of Welford et al., *Nucleic Acids Res.* 26(12):3059–3065 (1998), in which thousands of colonies produced using laborious traditional procedures were analyzed in an array, can be modified to make use of the disclosed method and thereby become more streamlined and efficient. The method could even be automated. Detection of differences between nucleic acid samples or probe sets can be accomplished by adapting the technique described by George et al., *Nucleic Acids Research* 27:1517–1523 (1999), to the disclosed method. George et al. describes combination of suppression subtractive hybridization (SSH) and cDNA microarrays for rapid identification of differentially expressed genes. In this method, a set of cDNA clones, including inserts amplified by PCR, is arrayed using robotic printing. The cDNA arrays can then be hybridized with fluorescent labeled probes prepared from RNA obtained from a cell line or tissue of interest.

H. Sequencing Amplified Nucleic Acid Molecules

The amplified nucleic acid can be sequenced using any suitable procedure. Many such procedures are known. One preferred form of sequencing for use with amplified sequences produced with the disclosed method is nanosequencing or single-nucleotide extension sequencing. Nanosequencing methods are described below and by Jalanko et al., *Clinical Chemistry* 38:39–43 (1992); Nikiforov et al., *Nucleic Acids Research* 22:4167–4175 (1994); and Kobayashi et al., *Molecular and Cellular Probes* 9:175–182 (1995).

Two forms of primer extension sequencing that can be used with the disclosed method are described in PCT Application WO 97/20948. One is single nucleotide primer extension sequencing involving interrogation of a single nucleotide in an amplified target sequence by incorporation of a specific and identifiable nucleotide based on the identity of the interrogated nucleotide. The other is degenerate probe primer extension sequencing involving sequential addition of degenerate probes to an interrogation primer hybridized to amplified target sequences.

Nanosequencing operations can be performed in batch. For example, if the slide contains 3000 dots, all 3000 dots are sequenced in a single batch operation. This can be accomplished by washing the slide with 1% ammonia after imaging of the first primer extension reaction. This alkaline solution denatures the labeled primer, but the cloned DNA remains on the slide because it is bound covalently. The subsequent primer extension reactions are performed, imaged, and washed with ammonia at each step until all five primers have been extended and the fluorescence incorporated by the primer has been imaged at each step.

The next step consists of determining a very short stretch of nucleotide sequence in the amplified DNA in each replica Each stretch of five bases is interrogated by using a mixture of specific primers for each base to be sequenced, using a single addition of a dideoxynucleotide triphosphate (ddNTP). The 3' end of the first primer (Primer 1) is positioned just before the first base to be sequenced. The sequence of the primer is defined by complementarity to vector sequences flanking the insert (or non-variable sequences flanking the region to be sequenced). The 3' end of the second primer (Primer 2) is positioned just before the second base to be sequenced. The sequence of the Primer 2 is defined by complementarity to the flanking sequences, but the last base at the 3' end is degenerate. A example design for Primer 1, Primer 2, and subsequent primers is shown below. The letter N indicates interrogation bases in a clone. The letter D indicates a degenerate base position in the primer. The question mark (?) indicates the nucleotide to be added to the primer.

```
Cloned sequence (SEQ ID NO:1):

TAAGTCTAGTTGACAGGATGCATGNNNNNNNNNtcagacagttgttgactgatggctg

ATTCAGATCAACTGTCCTACGTACNNNNNNNNNagtctgtcaacaactgactaccgac

Primer 1 (complexity = 1) (SEQ ID NOs:2 and 1)

TCTAGTTGACAGGATGCATG

ATTCAGATCAACTGTCCTACGTACNNNNNNNNNagtctgtcaacaactgactaccgac

Primer 2 (complexity = 4) (SEQ ID NOs:3 and 1)

CTAGTTGACAGGATGCATGD

ATTCAGATCAACTGTCCTACGTACNNNNNNNNNagtctgtcaacaactgactaccgac

Primer 3 (complexity = 16) (SEQ ID NOs:4 and 1)

TAGTTGACAGGATGCATGDD

ATTCAGATCAACTGTCCTACGTACNNNNNNNNNagtctgtcaacaactgactaccgac

Primer 4 (complexity = 64) (SEQ ID NOs: 5 and 1)

AGTTGACAGGATGCATGDDD

ATTCAGATCAACTGTCCTACGTACNNNNNNNNNagtctgtcaacaactgactaccgac

Primer 5 (complexity = 256) (SEQ ID NOs:6 and 1)

GTTGACAGGATGCATGDDDD

ATTCAGATCAACTGTCCTACGTACNNNNNNNNNagtctgtcaacaactgactaccgac
``` on the nitrocellulose. This entails sequencing just nine bases in a clone (which are referred to as the sequence tag of the clone). In this example, this is accomplished by two separate sets of sequencing reactions taking place in each replica-membrane. One set of sequencing reactions will determine the first five bases in the upper strand of the clone. The other set of sequencing reactions will determine the first five bases in the lower strand of the clone (always reading 5' to 3') as shown by the underlined X's below.

```
                    >>>>>
5'-NNNNNNNNNNNNNNNXXXXXXXXXNNNNNNNNNNNNNNNNNN-3'
3'-NNNNNNNNNNNNNNNXXXXXXXXXNNNNNNNNNNNNNNNNNN-5'
                    <<<<<
```

While primer 1 is not degenerate, primer 2 contains one degenerate position, primer 3 contains two degenerate positions, primer 4 contains three degenerate positions, and primer 5 contains four degenerate positions. Although primers 4 and 5 may prime at incorrect positions, the low complexity of the amplified DNA in a DNA colony produced by the disclosed method tends to ensure correct priming reads, on the average.

Primer extension is carried out for 5 minutes at 38° C. in a primer extension solution containing Primer 1 as the only primer. The primer extension mixture preferably contains a thermostable DNA polymerase such as Taq polymerase, and a mixture of four fluorescent dideoxy-oligodeoxyribonucleotides, each labeled with a different dye, as in standard fluorescent sequencing (Perkin Elmer-Applied Biosystems,Inc.). Because only dideoxynucleotides are present in each colony replica, and because the colony contains millions of copies of the nucleic acid sequence of interest, the added fluorescent label will be easily detectable for each reaction. After primer extension, the slide is washed to remove excess fluorescent ddNTPs, and imaged in a suitable fluorescence-imaging instrument capable of discriminating the four colors of the four different fluorescent dideoxy-oligodeoxyribonucleotides. Each DNA "colony" will light-up in a color corresponding to the base present at the interrogated position in each clone.

The procedure outlined above is then repeated another four times using subsequent primer sets (Primer 2, followed by Primer 3, and so on) in order to obtain the sequence at the next four positions. Signals are identified by coordinates of the clone, and the bases are ordered. The same procedure is carried out with the membrane replica, except using primers designed for sequencing the five bases in the sequence tag on the complementary strand. The use of the fifth primer (Primer 5) may be optimized, if required by performing a pre-hybridization and washing prior to primer extension. By making multiple replicas of a molecular clone array or spread, the entire primer extension sequencing procedure can be carried out in parallel by using ten replicas, five of which are used for primer extension in one direction, and five for primer extension in the opposite direction.

The order of the bases in a sequenced segment (that is, the sequence tag) can be used to identify each of the clones. The number of possible sequence segments containing nine bases (that is, the number of different sequence tags) is 262,144. It is thus desirable to use five different linear vectors, each containing a different restriction enzyme site or sticky ends. The use of five different linear vectors will increase the total number of possible sequence tags to 1,310,720. With this number of different sequence tags, it may be possible to identify uniquely up to 50,000 different mRNAs. Thus, as many as 50,000 expressed sequence tags (EST) may be distinguishable on the basis of their unique sequence using the disclosed method.

When the method is used for the sequencing of larger inserts, the situation is as follows:

from a single type of mRNA molecules. This can be accomplished, for example, as follows. First, a specific mRNA is amplified from any biological source using RT-PCR to obtain full-length amplification products. The amplified PCR product may have been derived from a mixture of wild-type sequence transcripts and also a small proportion (1/100, for example) of mutant transcripts that contain a single point mutation at a specific locus. Any other DNA fragment can also be used.

The PCR product is then nicked with DNAse I to generate a random population of DNA fragments. The DNA is nick-translated with Klenow DNA polymerase to generate a population of DNA fragments in the range of 120 to 200 nucleotides. This population of subsequences generated from the population of cDNA is then cloned into linear vectors to form circular vectors and the strands of the circular vectors separated as described herein. Vectors with inserts in the size range of 120 to 200 base pairs can be isolated (preferably before strand separation) by gel electrophoresis, or, preferably, by chromatography in Mono-Q 5/5/ (Pharmacia-LKB). The circular vectors are then amplified as described herein and the sequence of the ends of the inserts (which are thus the sequence tags) is determined as described above.

The sequence tags obtained from each clone consist of two pentamer (or even two hexamer) sequences. These sequence tags, which are known to be separated by segments of 120 to 200 bases, are catalogued and assembled into a contiguous sequence using techniques developed for hybridization sequencing. Starting with a cDNA product of a single type of mRNA, the cDNA can be entirely sequenced by assembling a catalog of sequenced clones. The sequence obtained from each clone is a pair of non-adjacent pentamers or hexamers.

When a large number of molecular clones are analyzed, the method can reveal the presence of point mutations, even if they are present as 1/100th of the cDNA population.

Starting with a complex mixture of cDNAs, small DNA segments (sequence tags) present in clones that originated

```
            >>>>>
5'-NNNNNNNNNNNNNNNNXXXXXXXXXX..//..XXXXXXXXXXNNNNNNNNNNNNNNNNN-3'
3'-NNNNNNNNNNNNNNNNXXXXXXXXXX..//..XXXXXXXXXXNNNNNNNNNNNNNNNNN-5'
                                   <<<<<
```

The short five-base sequences on each end, together with the sequences of flanking restriction enzyme sites, are sufficient to serve the function of unique tagging of each cDNA clone using the procedures described above.

Replica-binding of amplified nucleic acid molecules to glass slides, as described elsewhere herein, enables sequencing using a single slide. This is accomplished by washing the slide with 1% ammonia after imaging of the first primer extension reaction. This alkaline solution denatures the labeled primer, but the cloned nucleic acid remains on the slide because it is bound covalently. The subsequent primer extension reactions are performed, imaged, and washed with ammonia at each step until all five primers have been extended and the fluorescence incorporated by the primer has been imaged at each step.

An alternative method to read the output of nanosequencing reactions is to use mass spectroscopy instead of fluorescence. The use of mass spectroscopy for sequence identification of primers that have been extended by only one base has been described by Haff and Smirnov, *Genome Research* 7: 378–388 (1997).

The sequencing scheme shown above can permit the sequencing of a population of cDNA molecules derived from individual cDNA molecules in the cDNA population can be sequenced in situ using a similar procedure. The method can be scaled up by increasing the density of molecular colonies, and the number of colony replicas.

I. Illustrations of the Method

The disclosed method is further illustrated by the following examples.

Illustration 1: Cloning Using a Linker

A DNA sample is amplified by PCR using standard procedures, except that both oligonucleotide primers are designed to contain unique restriction enzyme sites, such that after amplification the PCR product may be cleaved, generating different sticky ends on each side of the linear DNA product. One of the PCR primers additionally contains a spacer sequence. The digested PCR product is then placed in a ligation mixture containing linkers designed to circularize the amplified DNA. The linkers represent the linear vector. The linkers are designed with a chemically modified terminus in one of the oligonucleotides, such that after ligation the resulting circular DNA molecules (that is circular vectors) will contain a single nick (or several nicks, if more than one linker is incorporated by ligation) in one of the strands. The modifier group may be a biotin, and it may be located either at the 5' or the 3' end of one of the linker oligonucleotides.

One of the PCR primers can also contain additional non-priming sequence designed to constitute the small spacer or backbone of the circular vector to allow amplification by rolling circle replication. The spacer sequence preferably contains a site for a rare-cutter restriction enzyme, which can be used to regenerate circles from linear DNA produced by amplification.

Optionally, the continuous strand of the circular vector can be separated from the discontinuous strand and unligated vector pieces using a two-step procedure. First, the circular vector, which contains a biotin residue, is bound to beads containing streptavidin, in order to bind the vector via the biotin present in one of the DNA strands that comprise the circular vector. The beads are then washed with formamide at mildly alkaline pH. Under appropriate conditions, the circularized DNA, which contains an unligated nick site by design, separates into two DNA molecules. Thus, mild alkaline-formamide denaturation releases free single-stranded circles from the beads. The single-stranded circular molecules are then further purified by gel filtration or ion exchange (Mono-Q 5/5) chromatography in the presence of an alkaline buffer (15 mM NaOH). This purification step will remove small linear molecules that contaminate the circular vector (which contain inserted nucleic acid molecules). The purpose of the purification procedure is useful for selecting certain DNA size classes, because this is desirable in certain applications. This separation is optional and the procedure can be performed with out strand separation or purification.

Dilutions of the DNA are then mixed with a buffer containing two primers (at approximately 1 $\mu$Molar concentration) designed for strand displacement cascade amplification (that is, a secondary strand displacement primer and a rolling circle replication primer/tertiary strand displacement primer) and melted agarose at 60° C. The solution is overlayed on a petri dish to form a thin agarose layer (1.0% to 2% agarose), such that the concentration of circular DNA molecules is in the range of 500 to 5,000 per plate. Then enzymes and dNTPs required to initiate rolling circle replication are then added. The agarose film is incubated for 0.5 to 3 hours at 38° C. (if the enzyme used is exo-Klenow) or at 60° C. (if the enzyme used is exo (–) Bst or exo (–) Bca; Walker et al. (1992); Walker, IBC International Conference, December, 1996). At appropriate dilutions, molecular "colonies" clonally derived from single circular vectors bearing DNA that originated in the PCR-amplified product, will form in the thin film of agarose. The initial density of seed DNA molecules should be such that the molecular colonies do not overlap.

In a preferred embodiment, one of the primers used in the amplification reaction is capable of forming a secondary structure. By lowering the temperature from 60° C. to 50° C., this special primer forms a hairpin structure that interferes with priming while the other primer continues to function normally. As the amplification reaction is continued for another 45 minutes, a large proportion of the DNA product becomes single-stranded DNA generated by strand displacement driven by the single functional primer. In this way, during the latter phase of the amplification reaction a large proportion of the DNA contained in each colony becomes single-stranded.

After amplification, the agarose film is placed in a vacuum-blotting device with a membrane that contacts the bottom of the agarose film. Part of the DNA on the agarose film is vacuum-blotted onto the membrane. This generates a replica of the DNA colonies on the surface of the membrane. Blotting is carried out for a brief period of time, so that approximately half of the amplified DNA remains in the agarose.

In a preferred embodiment, the DNA from the colonies may be blotted to a CAM membrane, a special membrane that permits reversible binding of DNA. CAM is cellulose acetate membrane containing cystamine (2,2'-dithio-bis [ethylamine]). The membrane contains primary amino groups, positively charged below pH 9.5, that can be easily removed under mild reductive conditions. CAM has been used to reversibly capture DNA fragments separated by electrophoresis. CAM has been successfully used with DNA fragments ranging from 0.5 to 320 Kbp. CAMs with different group densities can be synthesized (up to 1.65 $\mu$mole/sq cm); CAM with 1 $\mu$mole amino/sq cm has a binding capacity of at least 10 $\mu$g DNA/sq cm. The standard elution conditions for DNA fragments up to 10 Kbp are: 2 hours at room temperature in 25 mM EDTA, 0.2 M NaCl, and 25 mM 2-mercaptoethanol. Larger fragments require higher concentrations of the reducing agent. The chemistry involved in the preparation of CAM is well established (see Sundberg and Porath, *J. Chromatog.* 90:87–98 (1974); Uy and Wolf, (1977)).

CAM is prepared in two steps: (1) Oxirane groups are introduced by reacting cellulose acetate membranes (0.45 $\mu$m) with variable concentrations (0 to 30% v:v; depending upon the final group density required) of 1,4-butanediol diglycidyl ether in 0.1 M NaOH containing 2 mg/ml sodium borohydride; the reaction is allowed to proceed for 16 hours at RT, with mild agitation. (2) Cystamine is then coupled to the oxirane-containing membrane by reacting with 0.1 M cystamine in 0.1 M sodium tetraborate buffer, pH 9.5, for 16 hours at 37° C. Newly synthesized CAM is fully stable for at least 120 days at 4° C. The content of both oxirane and amino groups can be easily determined by standard reactions.

The thin agarose gel containing amplified DNA molecular colonies may be stained with a sensitive dye such as SIBR-GREEN II (Molecular Probes) in order to localize the position of each colony. The coordinates of the colony position then serves to locate the position of the replicas on the membrane.

In order to recover DNA from a CAM membrane and obtain single-stranded DNA that can be sequenced by standard methods, the procedure is as follows: Molecular colonies are generated as described above to generate single-stranded DNA (embodiment using one specifically structured primer that is inactivated by lowering the temperature), blotted to a CAM membrane, then a small droplet of DNA elution buffer (25 mM EDTA, 0.2 M NaCl, and 25 mM 2-mercaptoethanol) is placed on top of the desired colony, releasing in a few minutes a large proportion of the DNA of that colony replica. The small droplet is then recovered and mixed with four volumes of a buffer containing a sequencing primer and a suitable sequencing mixture for standard Sanger dideoxy sequencing.

In order to recover DNA from a membrane and regenerate replicatable DNA circles that can be amplified in solution by rolling circle replication, or grown again as molecular colonies, the procedure is as follows: a small droplet of elution buffer (25 mM EDTA, 0.2 M NaCl, and 25 mM 2-mercaptoethanol) is placed on top of the desired colony, releasing in a few minutes a large proportion of the DNA of that colony. The small droplet is then recovered and mixed with four volumes of a buffer containing a restriction enzyme that will cleave the amplified DNA at the rare-cutter site that was designed into the spacer sequence of one of the original PCR primers. After inactivating the restriction enzyme, the DNA is treated very briefly with highly diluted alkaline phosphatase, in order to cause partial dephosphorylation of the termini of the cleaved DNA. After phosphatase inactivation, the DNA is diluted and ligated in the presence of T4 DNA ligase, thus regenerating closed circular molecules. A fraction of the re-circularized molecules will contain a single nick, resulting from dephosphorylated ligation junctions, and these molecules will be capable of initiating rolling circle replication and strand displacement cascade amplification reactions.

Illustration 2: Cloning Using a Y-vector

1. Vector design: This linear vector has a 3' protruding T residue at each end, so as to permit ligation with PCR products that contain a 3'-terminal A (generated during PCR) at each end. The panhandle or tail of the Y is formed by two oligonucleotides that together constitute the second strand of the linear vector. The longer oligonucleotide contains an oligo-dA sequence of 16 bases at the 3' terminus. The oligo-da sequence serves as an affinity tag (where the affinity target will be oligo-dT). The shorter oligonucleotide contains a 5' phosphate. Sequences of an example of a functional Y-vector are shown below.

K.58 (SEQ ID NO:7)

P-CATGAGGACTAGCAGATGGATGCGGCCGCAGCTCG

TGTAATACGACTCACTATAGGGT-3'

A.60 (SEQ ID NO:8)

P-CCCTATAGTGAGTCGTATTACACGAGCTGCTAGCAT

CATTAGCCAAAAAAAAAAAAAAAA-3

B.42 (SEQ ID NO:9)

P-GGCTAATGATGCTAGGCCGCATCCATCTGCTAGTCCTCATGT-3'

2. The Y-vector is assembled by incubation of oligonucleotide K.58, A.60 and B.42, for 5 minutes at 40° C., and then ligated with a mixture of PCR-amplicons using T4 DNA ligase at 16° C. for 16 hours, to generate circular vectors with inserts. Oligonucleotide K.58 is in the first strand (that is, continuous strand) of the circular vector. Oligonucleotides A.60 and B.42 are in the second strand (that is, the discontinuous strand) of the circular vector. Insert sequences are in both strands of the circular vector.

3. After ligation, the vectors with ligated inserts are incubated at room temperature with oligo-dT-cellulose (Life Sciences, Inc.) in the presence of DNA ligase. The oligo-dT-cellulose is an affinity substrate where the cellulose is the solid-state substrate and the oligo-dT is the affinity target. The Y-vector is ligated to the solid matrix via the panhandle sequence (the 5' end of B.42 is covalently bound to the 3' end of the oligo-dT on the oligo-dT-cellulose). The solid matrix is then washed with 20 mM Tris pH 8, 0.1 M NaCl, to remove unligated vectors.

4. The matrix is washed with 0.5 ml of 50 mM NaOH, releasing single-stranded circular DNA (the first strand of the circular vector) from the cellulose matrix. The now immobilized second strand of the circular vector remains attached to the cellulose matrix.

5. The circular vector is diluted serially to obtain concentrations in the range of several million circular vector molecules per milliliter. Approximately 22 µl of this DNA solution (containing approximately 30,000 to 120,000 DNA molecules) is placed on a cover slip, and covered with a polylysine-coated microscope slide. The DNA is allowed to bind to the polylysine-covered surface for 30 minutes at 37° C. The slide then dipped in 0.01% Tween-20, and dried at room temperature.

6. Using an arraying instrument, an array is constructed consisting of 6000 individual micro-droplets of a solution containing two suitable primers designed for the constant sequence domains of the Y-vector, compatible buffer, and polymerase (Large fragment Bst, or exo-Vent DNA polymerase) capable of supporting rolling circle replication.

Primer 1 (23) (SEQ ID NO: 10)
GCATCCATCTGCTAGTCCTCATG
Primer 2 (22) (SEQ ID NO: 11)
CGCAGCTCGTGTAATACGACTC Primer 1 serves as the rolling circle replication primer and a tertiary strand displacement primer. Primer 2 serves as a secondary strand displacement primer. The use of these primers will result in strand displacement cascade amplification. The diameter or the droplets should be approximately 0.150 to 0.200 millimeters. Droplets are dispensed on the surface of the slide in a controlled humidity atmosphere, in order to maintain a constant droplet volume for a period of 90 minutes. Alternatively, the diluted circular DNA molecules may be placed on the glass surface using the arrayer instrument to dispense small volumes of liquid that on the average contain a single ligated DNA molecule.

7. The array is incubated for 90 minutes at constant temperature (62° C.) to amplify any DNA molecules in contact with (or within) the droplets. When 33% of the droplets grow DNA colonies, and the rest do not grow anything, most colonies are likely to be of clonal origin. Adjusting the initial inoculum density, it should be possible to obtain up to 1500 clonal colonies per 6000-droplet array.

Optionally, the amplified nucleic acid can be replica plated in order to save a copy of the clones or to perform additional operations on the clones. In order to facilitate replica plating (via covalent binding to a glass surface), each of the two primers used for the strand displacement cascade amplification of the circular vectors may be synthesized with a primary amino group at the 5' end. At the end of the SDCA reaction, a glass slide is placed over the glass slide with the reaction droplets leaving an air gap of less than 1 mm (defined by the thickness of a plastic spacer) in such a manner that the glass on top will contact all of the liquid droplets without excessive compression. Prior to use, the lower face of this slide (the upper slide) is derivatized using the methods described by Guo et al., *Nucleic Acids Research* 22;5456–5465 (1994), and Guo et al., *Nature Biotechnology* 15:331–335 (1997)), to make the glass surface chemically reactive with amino groups. The two-slide sandwich is incubated for 1 to 2 hours at 37° C. in order to obtain covalent coupling of the amplified DNA contained in each droplet to the lower face of the upper slide.

8. DNA colonies may be identified by staining with the dye Sybr-Green-I (Molecular Probes, Inc.). Alternatively, replica slides may be made as indicated above, and used for any desired microarray hybridization experiment. The DNA in each colony may also be isolated and identified or analyzed by DNA sequencing.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

I claim:

1. A method of isolating and amplifying a nucleic acid molecule, the method comprising (a) ligating a nucleic acid molecule into a linear vector to form a circular vector comprising the vector and the nucleic acid molecule, wherein the linear vector is a double-stranded linear nucleic acid comprising two nucleic acid strands, wherein the second strand of the circular vector is discontinuous, and wherein the first strand in the circular vector is a closed circular strand, (b) amplifying the first strand by rolling circle replication to form tandem sequence DNA, wherein the amplification results in amplification of the nucleic acid molecule in the first strand.

2. The method of claim 1 wherein the second strand of the linear vector contains at least one nick, wherein the nick cannot be ligated.

3. The method of claim 1 wherein either the 5' or the 3' end of the second strand of the linear vector cannot be ligated.

4. The method of claim 1 wherein the second strand of the linear vector contains at least one gap or overlap.

5. The method of claim 1 wherein the method further comprises, following ligation and prior to amplification, separating the first strand from the second strand.

6. The method of claim 5 wherein the second strand includes an affinity tag.

7. The method of claim 6 wherein the first strand is separated from the second strand by binding the affinity tag to a substrate, denaturing the first and second strands prior to, simultaneous with, or following binding, and separating the first strand from the substrate.

8. The method of claim 5 wherein the second strand of the linear vector contains at least one overlap, part of the overlapping portions of the second strand are complementary, and the 3' end of the overlap extends beyond the part of the overlapping portions that are complementary, wherein the first strand is separated from the second strand by ligating one end of the second strand to a nucleic acid molecule coupled to a substrate, denaturing the first and second strands following ligation of the second strand, and separating the first strand from the substrate.

9. The method of claim 1 wherein step (a) comprises ligating a plurality of nucleic acid molecules into a plurality of linear vectors in a single reaction to form a plurality of circular vectors, each circular vector containing at least one nick, gap, or overlap in the second strand, wherein step (b) comprises amplifying the first strand of the plurality of circular vectors, and wherein the method further comprises, prior to amplification, dividing the ligation reaction to produce a plurality of separate amplification reactions.

10. The method of claim 9 further comprising making a replica of the amplification reactions.

11. The method of claim 10 wherein the replica of the amplification reactions is made by contacting the amplification reactions with a surface to which nucleic acids can bind.

12. The method of claim 10 wherein the replica of the amplification reactions is made by transferring part of each amplification reaction to form a replica amplification reaction.

13. The method of claim 9 wherein the ligation reaction is divided by spreading the ligation reaction onto a surface to form a spread, and wherein the separate amplification reactions are the locations of circular vectors on the surface after spreading.

14. The method of claim 13 further comprising making a replica of the amplification reactions.

15. The method of claim 14 wherein the replica is made by contacting the spread with a second surface to which nucleic acids can bind.

16. The method of claim 9 wherein any number or all of the amplification reactions are ordered as an array of reaction droplets or in an array of reaction vessels.

17. The method of claim 16 wherein, following amplification, all or part of the contents of any number or all the individual reaction droplets or reaction vessels are transferred by one to one mapping to a new set of reaction droplets or reaction vessels.

18. The method of claim 17 further comprising, following amplification, determining the presence of amplified nucleic acid in the amplification reactions, and transferring all or a part of the contents of the amplification reactions containing amplified nucleic acid reaction to a new set of reaction droplets or by reaction vessels.

19. The method of claim 16 further comprising making a replica of the amplification reactions.

20. The method of claim 19 wherein the replica of the amplification reactions is made by contacting the amplification reactions with a surface to which nucleic acids can bind.

21. The method of claim 19 wherein the replica of the amplification reactions is made by contacting the amplification reactions with a surface treated with an affinity target capable of binding an affinity tag, wherein the amplified nucleic comprises affinity tags incorporated during amplification, wherein a portion of each amplification reaction is transferred to the surface.

22. The method of claim 21 wherein the affinity tag is biotin and the affinity target is streptavidin.

23. The method of claim 21 wherein the affinity tag is a reactive moiety and the affinity target is a corresponding reactive moiety, where a chemical reaction between the affinity tag and the affinity target results in the amplified nucleic acid being covalently coupled to the surface.

24. The method of claim 23 wherein the affinity target is phenylene diisothiocyanate, disuccinimidylcarbonate, disuccinimidyloxolate or dimethylsuberimidate and the affinity tag is a reactive amine.

25. The method of claim 19 wherein the replica of the amplification reactions is made by transferring part of each amplification reaction to form a replica amplification reaction.

26. The method of claim 16 wherein, following amplification, all or part of the contents of any number or all of the reaction droplets or reaction vessels are transferred and combined to create one or more sets of pooled reactions.

27. The method of claim 16 wherein the amplification reactions are arranged on the surface of a substrate.

28. The method of claim 27 wherein the substrate comprises acrylamide, cellulose, nitrocellulose, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, polyamino acids, chemical resistant metals, or corrosion resistant metals.

29. The method of claim 9 wherein the method further comprises, prior to dividing the ligation reaction, diluting the ligation reaction such that, on average, each amplification reaction contains a single circular vector.

30. The method of claim 9 wherein the method further comprises, following amplification, collecting a sample of each amplification reaction.

31. The method of claim 9 wherein the method further comprises detecting or sequencing the nucleic acid molecules in the amplification reactions or in the collected samples.

32. The method of claim 1 wherein rolling circle replication is primed by the second strand.

33. The method of claim 1 wherein rolling circle replication is primed by a rolling circle replication primer.

34. The method of claim 33 wherein the tandem sequence DNA is amplified by strand displacement replication to form secondary tandem sequence DNA.

35. The method of claim 34 wherein the secondary tandem sequence DNA is amplified by strand displacement replication to form tertiary tandem sequence DNA.

36. The method of claim 34 wherein strand displacement replication of the tandem sequence is primed by a strand displacement primer.

37. The method of claim 9 further comprising detecting one or more amplified nucleic acid molecules in one or more of the amplification reactions.

38. The method of claim 37 wherein the nucleic acid molecules are derived from cDNA generated by suppression subtractive hybridization.

39. The method of claim 37 wherein the plurality of nucleic acid molecules are all derived from the same source.

40. The method of claim 37 further comprising, following amplification, creating a replica of the amplification reactions, contacting the amplification reactions with a first set of labeled nucleic acid probes and the replica amplification reactions with a second set of labeled nucleic acid probes, and comparing the pattern of hybridization of the first set of probes to the pattern of hybridization of the second set of probes, wherein differences in the patterns of hybridization indicate differences in the probe sets.

41. The method of claim 40 further comprising selecting for isolation or further analysis amplification reactions that hybridize to the first set of probes but not to the second set of probes, amplification reactions that hybridize to the second set of probes but not to the first set of probes, amplification reactions that hybridize to the both sets of probes, or amplification reactions that do not hybridize to either set of probes.

42. A method of isolating and amplifying nucleic acid molecules, the method comprising (a) ligating a plurality of nucleic acid molecules into a plurality of linear vectors in a single reaction to form a plurality of circular vectors, each circular vector comprising a vector and a nucleic acid molecule, wherein the linear vectors are double-stranded linear nucleic acid comprising two nucleic acid strands, wherein the circular vectors each contain at least one nick, gap, or overlap in the second strand, and wherein the first strand in each circular vector is a closed circular strand, (b) separating the first strands from the second strands, (c) diluting and dividing the first strands to produce a plurality of separate amplification reactions that, on average, each contain a single circular vector, (d) amplifying the first strands of the plurality of circular vectors by rolling circle replication to form tandem sequence DNA, wherein the amplification results in amplification of the nucleic acid molecules in the first strands.

43. The method of claim 42 wherein the tandem sequence DNA is amplified by strand displacement replication to form secondary tandem sequence DNA.

44. The method of claim 43 wherein the secondary tandem sequence DNA is amplified by strand displacement replication to form tertiary tandem sequence DNA.

45. A method of isolating and amplifying a nucleic acid molecule, the method comprising (a) ligating a nucleic acid molecule into a linear vector to form a circular vector comprising the vector and the nucleic acid molecule, wherein the linear vector is a double-stranded linear nucleic acid comprising two nucleic acid strands, wherein the circular vector contains at least one nick in the second strand and wherein the first strand in the circular vector is a closed circular strand, (b) amplifying the first strand, wherein the amplification results in amplification of the nucleic acid molecule in the first strand.

* * * * *

SEQUENCE LISTING

```
<160> NUMBER OF SEQ ID NOS:  11

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Cloned
      sequence
<221> NAME/KEY: misc_feature
<222> LOCATION: (25)..(33)
<223> OTHER INFORMATION: N indicates interrogation bases in a clone and
      is either A, T, G, or C

<400> SEQUENCE: 1
taagtctagt tgacaggatg catgnnnnnn nnntcagaca gttgttgact gatggctg         58

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (21)
<223> OTHER INFORMATION: N represents the nucleotide added to the primer
      and is either A, G, C, ot T

<400> SEQUENCE: 2
tctagttgac aggatgcatg n                                                 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (21)
<223> OTHER INFORMATION: N represents the nucleotide added to the primer
      and is either A, G, C, ot T
<221> NAME/KEY: misc_feature
<222> LOCATION: (20)
<223> OTHER INFORMATION: N represents a degenerate base position in the
      primer

<400> SEQUENCE: 3
ctagttgaca ggatgcatgn n                                                 21
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (21)
<223> OTHER INFORMATION: N represents the nucleotide added to the primer
      and is either A, G, C, ot T
<221> NAME/KEY: misc_feature
<222> LOCATION: (19)..(20)
<223> OTHER INFORMATION: N represents a degenerate base position in the
      primer

<400> SEQUENCE: 4
tagttgacag gatgcatgnn n                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (21)
<223> OTHER INFORMATION: N represents the nucleotide added to the primer
      and is either A, G, C, ot T
<221> NAME/KEY: misc_feature
<222> LOCATION: (18)..(20)
<223> OTHER INFORMATION: N represents a degenerate base position in the
      primer

<400> SEQUENCE: 5
agttgacagg atgcatgnnn n                                        21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (21)
<223> OTHER INFORMATION: N represents the nucleotide added to the primer
      and is either A, G, C, ot T
<221> NAME/KEY: misc_feature
<222> LOCATION: (17)..(20)
<223> OTHER INFORMATION: N represents a degenerate base position in the
      primer

<400> SEQUENCE: 6
gttgacagga tgcatgnnnn n                                        21

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
catgaggact agcagatgga tgcggccgca gctcgtgtaa tacgactcac tataggggt      58

<210> SEQ ID NO 8
<211> LENGTH: 60
<212> TYPE: DNA
<213> ORGANISM: Artificial Sequence
<220> FEATURE:

-continued

```
<223> OTHER INFORMATION: Description of Artificial Sequence:
      Oligonucleotide

<400> SEQUENCE: 8
ccctatagtg agtcgtatta cacgagctgc tagcatcatt agccaaaaaa aaaaaaaaaa         60

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ggctaatgat gctaggccgc atccatctgc tagtcctcat gt                           42

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
gcatccatct gctagtcctc atg                                                23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
cgcagctcgt gtaatacgac tc                                                 22
```